United States Patent [19]

Avjioglu et al.

[11] Patent Number: 5,691,167
[45] Date of Patent: Nov. 25, 1997

[54] DNA ENCODING ALLERGENIC PROTEINS AND PEPTIDES FROM JOHNSON GRASS POLLEN

[75] Inventors: Asil Avjioglu, Towson, Md.; Mohan Bir Singh; Robert Bruce Knox, both of Victoria, Australia

[73] Assignees: The University of Melbourne, Parkville, Australia; ImmuLogic Pharmaceutical Corporation, Waltham, Mass.

[21] Appl. No.: 175,096

[22] Filed: Dec. 29, 1993

Related U.S. Application Data

[62] Division of Ser. No. 971,096, Oct. 30, 1992, Pat. No. 5,480,972.

[51] Int. Cl.$^6$ ............................. C12P 21/02; C12N 1/21; C12N 15/63; C07H 21/04
[52] U.S. Cl. .................. 435/69.3; 435/252.3; 435/320.1; 536/23.6
[58] Field of Search ........................ 435/69.3, 320.1, 435/240.1, 252.3; 536/23.6

[56] References Cited

FOREIGN PATENT DOCUMENTS

| | | |
|---|---|---|
| 31644/89 | 9/1989 | Australia. |
| 89/09260 | 10/1989 | WIPO. |
| WO 92/03550 | 3/1992 | WIPO. |
| WO9216554 | 10/1992 | WIPO. |
| WO93/01213 | 1/1993 | WIPO. |

OTHER PUBLICATIONS

Gould et al. (1989) PNAS USA 86, 1934–1938.
Griffith et al. (1991) FEBS Lett. 279(2), 210–215.
Helfman et al. (1987) in "Methods in Enzymol., vol. 152" ed. Berger et al. pp. 451–457, Academic Press, N.Y.
Singh et al. (1985). Int. Archs. Allergy Appl. Immun. 78, 300–304.
Livingstone, A.M. et al. (1987) "The structure of T–cell epitopes" Ann. Rev. Immunol. 5:477–501, 1987.
Watson et al., *JAMA*, 78:718–722, 1992.
French, *J. Allergy*, 1:286–291, 1930.
Martin et al., *Annals of Allergy*, 54:99–104, 1985.
Yoo et al.,*Annals of Allergy*, 39:272–275, 1977.
Ruffin et al., *Environ. & Experim. Botany*, 23(4):311–319, 1983.
Matthiesen et al., *J. Allergy Clin. Immunol.*, 88(5):763–774, 1991.
Lowenstein et al., *J. Allergy Clin. Immunol.*, 89:151, 1992.
Hulbert et al., *Proc. Natl. Acad. Sci. USA*, 87:4251–4255, 1990.
Hoang–Tang et al., *Genome*, 34:251–250, 1991.

*Primary Examiner*—Robert A. Wax
*Assistant Examiner*—Kawai Lau
*Attorney, Agent, or Firm*—Lahive & Cockfield, LLP; Jane E. Remillard; Amy E. Mandragouras

[57] ABSTRACT

The present invention provides a nucleic acid having a nucleotide sequence coding for Sor h I, a major allergen of *Sorghum halepense*, and fragments thereof. The present invention also provides purified Sor h I or at least one fragment thereof, produced in a host cell transformed with a nucleic acid sequence coding for Sor h I, or at least one fragment thereof and fragments of Sor h prepared synthetically. Sor h I and fragments thereof are useful for diagnosing, treating, and preventing allergy to Johnson grass pollen.

13 Claims, 12 Drawing Sheets

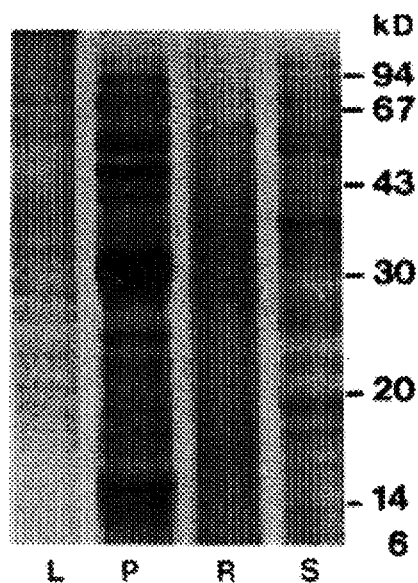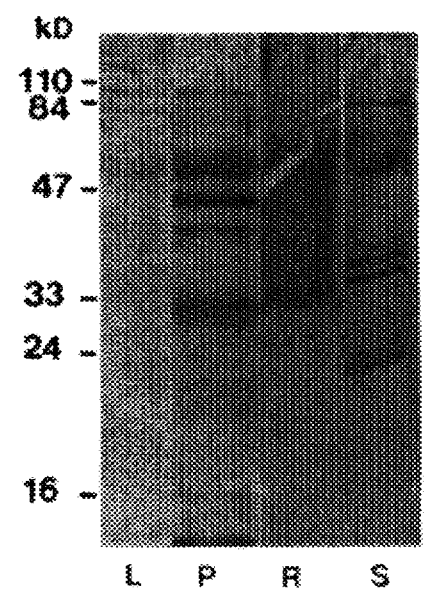
Fig. 1A  Fig. 1B
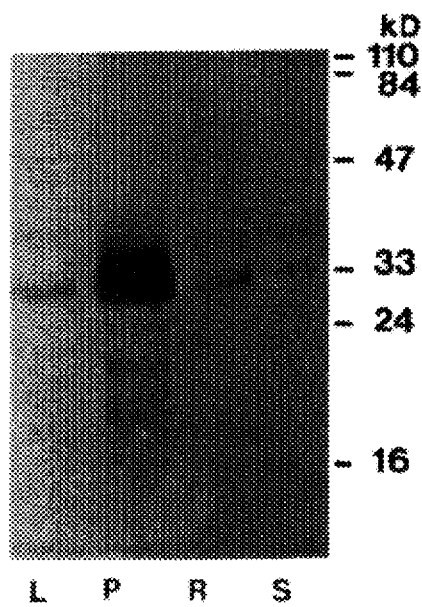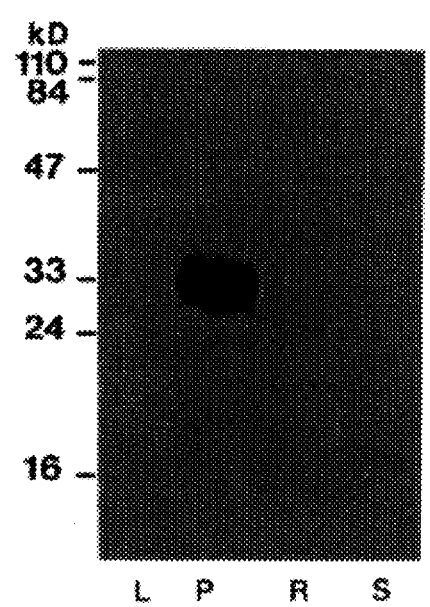
Fig. 1C  Fig. 1D

```
                                              GCGGCCGCAAACGATCGAAGGAAGATGGAGTGAACATG    35
                  -20                    -10
        M   S   W   S   M   Q   V   A   L   V   V   A   L   A   F   L   V   G   G   A
       ATGTCGTGGTCGATGCAGGTGGCCTTGGTGGTGGCCTTGGCGCTGGCGTTTCTGGTGGGCGGCGCA                99
        1                       10
        W   C   G   P   P   K   V   A   P   G   K   N   I   T   A   T   Y   G   S   D
       TGGTGCGGTCCTCCCAAGGTTGCCCCGGGCAAGAACATCACGGCCACCTACGGCAGCGAC                     159
       20          30
        W   L   E   R   K   A   T   W   Y   G   K   P   T   G   A   G   P   D   D   N
       TGGCTGGAACGGAAGGCAACATGGTACGGTAAGCCAACAGGTGCCGGCCCCGACGACAAC                     219
               40                      50
        G   G   A   C   G   Y   K   D   V   N   K   A   P   F   N   S   M   G   A   C
       GGCGGCGGCGCATGTGGTTACAAGGATGTGAACAAGGCCCCCTTCAACAGCATGGGCGCGTGC                  279
           60                      70
        G   N   L   P   I   F   F   K   D   G   L   G   C   G   S   C   F   E   I   K   C
       GGCAACCTCCCCATCTTCAAGGACGGGCCTCGGCTGCGGCTCCTGCTTTGAGATCAAGTGT                    339
           80                      90
        D   K   P   A   E   C   S   G   E   A   V   V   V   H   I   T   D   M   N   Y
       GACAAGCCGGCCGAGTGCTCCGGGGAGGCCGTGGTGGTGCACATCACGGACATGAACTAC                     399
           100                     110
        E   Q   I   A   A   Y   H   F   D   L   A   G   T   A   F   G   A   M   A   K
       GAGCAAATCGCCGCCTACCACTTCGACCTGGCCGGCACGGCGTTCGGGGCCATGGCCAAG                     459
```

Fig. 5A

```
          120                      130
    K  G  E  E  E  K  L  R  K  A  G  I  I  D  M  K  F  R  R  V
    AAGGGCGAGGAGGAGAAGCTGCGCAAGGCGGGCATCATCGACATGAAGTTCCGCCGGGTC    519

140                      150
    K  C  K  Y  G  E  K  V  T  F  H  V  E  K  G  S  N  P  N  Y
    AAGTGCAAGTACGGCGAAAAGGTCACCTTCCACGTGGAGAAGGGAGCAACCCCAACTAC    579

160                      170
    L  A  L  L  V  K  Y  Y  V  D  G  D  G  D  V  V  G  V  D  I  K
    CTGGCTCTCGTTGGTCAAGTACGTCGACGGCGACGGTGACGTTGTGGGGGTGACATCAAG    639

180                      190
    E  K  G  G  D  A  Y  Q  P  L  K  H  S  W  G  A  I  W  R  K
    GAGAAGGGTGGCGACGCGTACCAGCCCCTCAAGCACTCCTGGGGCGCTATCTGGAGGAAG    699

200                      210
    D  S  D  K  P  I  K  F  P  V  T  V  Q  I  T  T  E  G  G  T
    GACAGCGACAAGCCAATCAAGTTTCCCGTCACCGTCCAAATCACCACCGAGGGAGGCACC    759

220                      230
    K  T  A  Y  E  D  V  I  P  E  G  W  K  A  D  T  T  Y  T  A
    AAGACCGCCTACGAAGACGTCATCCCCGAAGGCTGGAAGGCCGACACCACCTACACCGCC    814

K  *
    AAGTAAACTGTCCAACAGACCTAACGCTGCTCTGGCTCGGTTGGATTGGATCCCAACTT    879
    CCCAAGCAATGCATTACACTTACGCATGCATGCATCGATCCACAATGCACATATATTTTTAC    939
    TGCTGCTACTGCTACGACAATGTCCTCCTCTTGTCCTCCATATATAGCTAGAGTCAGGC    999
    TCCGCTCTCTTATATTATTATTATTATATAAGATAAGAAATAGGAGAGAGAGACCG    1059
    AGTAAGCGGGCGG                                                 1072
```

Fig. 5B

```
                                                CATTAAGCAGCAACCAACAAATTCAAGACAAG         32
                                GCGGCCGCAAACGATCGAAGGAAGATGGGAGTGAACATG                  39

Lol p I   ATG GCG TCC TCC TCG GTG CTC CTG GTG GCG CTG TTC GCC                           77
Sor h I   ... T.. .GG ..G AT. CA. GCG T.. ... ... ... GCG TTT                            84

Lol p I   GTG TTC CTG GGC ATC GCG AAG GTA CCA CCG GGC                                    122
Sor h I   C.. G.G GGC ... GCA TG. TGC ..T CCT C.C ..T G.C ...                            129

Lol p I   CCC AAC ATC ACG GCC GAG TAC GGC GAC AAG TGG CTG GAC GCG AAG                    167
Sor h I   AAG ... ... ... ... ACC ... AG. ... ..A CG. ...                                174

Lol p I   AGC ACC TGG TAT GGC AAG CCG ACC GCC GGT CCC AAG GAC AAC                        212
Sor h I   GCA ..A ... ..C ... ..T ... ..A ..A ..C ... G.C ...                            219

Lol p I   GGC GCG TGC TGC TAC AAG GAC GTC GAC AAG GCG CCG TTC AAC                        257
Sor h I   ... ... ..A ..T ... ... ..T .G A. ... ... ..C ..C                              264

Lol p I   GGC ATG ACC GGC TGC GGG AAC ACC CCC ATC TTC AAG GAC GGC CGT                    302
Sor h I   A.. ... GG. .CG ... ... CT. ... ... ... ... ... ... ..TC                       309

Lol p I   GGC TGC GGC TCC TGC TTC GAG ATC AAG TGC ACC AAG CCC GAG TCC                    347
Sor h I   ... ... ... ... ... ..T ... ... ..T GA. ... ..G ..CC GAG                       354

Lol p I   TGC TCC GGC GAG GCT ACC GTC ACA ATC ACC GAC GAC AAT GAG                        392
Sor h I   ... ... ... ... ..C ... ..G GTG ..G CAC ... ..G ATG ..C T.C                    399

Lol p I   GAG CCT ATC GCA CCC TAC CAC TTC GAC CTC TCG GGC CAC TTC                        437
Sor h I   ... ... .AA ... ..C G.. ... ... ... ... ... .G G.C ACG ..G                     444
```

Fig. 7A

| | | | | | | | | | | | |
|---|---|---|---|---|---|---|---|---|---|---|---|
| Lol p I | GGC TCC ATG GCG AAG AAG AAG GGC GAG GAG CAG AAG CTC CGC AGC GCC | 482 |
| Sor h I | ..C G.. ... ... ... ... ... ... ... ... ... G.. ... ... .AG ..G | 489 |
| | | |
| Lol p I | GGC GAG CTG GAG CTC CAG TTC AGG CGG GTC AAG TGC AAG TAC CCG | 527 |
| Sor h I | ... ATC A.C ..C A.G A.. ... ... C.C ... ... ... ... ... ... | 531 |
| | | |
| Lol p I | GAC GGC ACC AAG CCG ACA TTC CAC GTC GAG AAG GCT TCC AAC CCC | 572 |
| Sor h I | ... GAA ... GTC ..C ... ... ..G ... ... ... .GG AG. ... ... | 573 |
| | | |
| Lol p I | AAC TAC CTC GCT ATT CTG GTG AAG TAC GTC GAG GGC GAG GGT CAG | 617 |
| Sor h I | ... ... ..G ... C.G T.. ..C ... ... ... ... ... ... ... ... | 618 |
| | | |
| Lol p I | GTG GTG GCG GTG GAC ATC AAG GAG AAG GGC AAG GAT AAG TGG ATC | 662 |
| Sor h I | ..T .G. ... ... ... ... ... ... ... ..T GGC ..C GC. .AC CAG | 663 |
| | | |
| Lol p I | GAG CTC AAG GAG TCG TGG GGA GCA GTC TGG AGG ATC GAC ACAC CCC | 707 |
| Sor h I | CCC ... ... C.C ..C ... ... ..C ..T A.. ... .AG ... .G. GA. | 708 |
| | | |
| Lol p I | GAT AAG CTG ACG GGC CCA TTC ACC GTC CGC TAC ACC ACC GAG GGC | 752 |
| Sor h I | A.G CCA A.C .A. TTT ..C G.. ... ... .AA AT. ... ... ... ..A | 753 |
| | | |
| Lol p I | GGC ACC AAA TCC GAA GTC GAG GAT GTC ATC CCT GAG GGC TGG AAG | 797 |
| Sor h I | ... ... .G A.. .CC TA. ...A ..C ... ... ..C ..A ... ... ... | 798 |
| | | |
| Lol p I | GCC GAC ACC TCC TAC TCG GCC AAG TGA GCAAGAAGTGGAGTGATCTTCTT | 847 |
| Sor h I | ... ... A.. ... A... A.C ... .A .A. ACTGTCCAACAGACCTAACGCTG | 848 |
| | | |
| Lol p I | CCAATCAGCTTAATTTTGACTCAAGATCTCAAATAATCCAGCCGCACATATATACGAGG | 906 |
| Sor h I | CTCTGGGCTCGGTTGGATTGGAGTCCCAACTTCCCAAGCAATGCATTACACTTACGCATG | 907 |

Fig. 7B

| Lol p I | CGGTGAGACATACAAGCTCCTCCATGAGTATATTCATTCATGCCGTATAGAGAGGAGAA | 965 |
| Sor h I | CATCGATCCATGCACAATATCTATTTTTTACTGCTGCTACTGCTACGACAATGTCCTC | 966 |
| Lol p I | AGATGCCTGAATAAGAGTTTGAGGTCGACACCTTGTGAGAAGTGTATATAGGAGAACC | 1024 |
| Sor h I | CTTTGTCCTCTCCATATATAGCTAGAGTCAGGCTCCGCTCTCTTATATTATTATTATAT | 1025 |
| Lol p I | CAATCTGGCTCCATCTTTCTTTGCTCGCACGGTGTACTGCTAAGGTTATCTTTCTAACAG | 1083 |
| Sor h I | AAGATAAGAAATAGGAGAGAGAGACCGAGTAAGCGGGCGG | 1072 |
| Lol p I | GCCAGATTAACCTACTATCTAATATATGCAACGTATGGTCATTTTCCCTAAAAAAA | 1139 |

Fig. 7C

```
Lol p I    MASSSSVLLVVALFAVFLGSAHGIAKVPPGPNITAEYGDKWLDAKSTWYGKPT
           ::S : : :::::: S ::S : :: :::::: :: ::S:::::::
Sor h I    MSWSMQVALVVALAFLVGGAWCGPPKVAPGKNITATYGSDWLERKATWYGKPT

Lol p I    GAGPKDNGGACGYKDVDKAPFNGMTGCGNTPIFKDGRGCGSCFEIKCTKPESC
           ::: ::::::::::: ::::::: :: ::::: ::::::::::::: ::  .
Sor h I    GAGPDDNGGACGYKDVNKAPFNSMGACGNLPIFKDGLGCGSCFEIKCDKPAEC

Lol p I    SGEAVTVTITDDNEEPIAPYHFDLSGHAFGSMAKKGEEQKLRSAGELELQFRR
           :::::: :: :: :::::: .. :::::S::::::: :: SSS ::: ::
Sor h I    SGEAVVVHITDMNYEQIAAYHFDLAGTAFGAMAKKGEEEKLRKAGIIDMKFRR

Lol p I    VKCKYPDGTKPTFHVEKASNPNYLAILVKYVDGDGDVVAVDIKEKGKDKWIEL
           ::: :: :: ::::::::::::::S::::::::::::::::::::::: S :
Sor h I    VKCKY**GEKVTFHVEKGSNPNYLALLVKYVDGDGDVVGVDIKEKGGDAYQPL

Lol p I    KESWGAVWRIDTPDKLTGPFTVRYTTEGGTKSEVEDVIPEGWKADTSYSAK
           : ::::S:: :S  S  ::  : :::::::S ::::::::::S:S::
Sor h I    KHSWGAIWRKDSDKPIKFPVTVQITTEGGTKTAYEDVIPEGWKADTTYTAK
```

DNA ENCODING ALLERGENIC PROTEINS AND PEPTIDES FROM JOHNSON GRASS POLLEN

This application is a division of application Ser. No. 07/971,096, filed on Oct. 30, 1992 now U.S. Pat. No. 5,480,972.

BACKGROUND OF THE INVENTION

Genetically predisposed individuals, who make up about 10% of the population, become hypersensitized (allergic) to antigens from a variety of environmental sources to which they are exposed. Those antigens that can induce immediate and/or delayed types of hypersensitivity are known as allergens. (King, T. P., Adv. Immunol. 23:77–105, (1976)). Anaphylaxis or atopy, which includes the symptoms of hay fever, asthma, and hives, is one form of immediate allergy. It can be caused by a variety of atopic allergens, such as products of grasses, trees, weeds, animal dander, insects, food, drugs, and chemicals.

The antibodies involved in atopic allergy belong primarily to the IgE class of immunoglobulins. IgE binds to mast cells and basophils. Upon combination of a specific allergen with IgE bound to mast cells or basophils, the IgE may be cross-linked on the cell surface, resulting in the physiological effects of IgE-antigen interaction. These physiological effects include the release of, among other substances, histamine, serotonin, heparin, a chemotactic factor for eosinophilic leukocytes and/or the leukotrienes, C4, D4, and E4, which cause prolonged constriction of bronchial smooth muscle cells (Hood, L. E. et al. Immunology (2nd ed.), The Benjamin/Cumming Publishing Co., Inc. (1984)). These released substances are the mediators which result in allergic symptoms caused by a combination of IgE with a specific allergen. Through them, the effects of an allergen are manifested. Such effects may be systemic or local in nature, depending on the route by which the antigen entered the body and the pattern of deposition of IgE on mast cells or basophils. Local manifestations generally occur on epithelial surfaces in the location at which the allergen entered the body. Systemic effects can include anaphylaxis (anaphylactic shock), which is the result of an IgE-basophil response to circulating (intravascular) antigen.

The sub-tropical grass *Sorghum halepense* (Johnson grass) is representative of a genus which is widely cultivated as a cereal grain plant. Sorghums are the major cereal grain cropped in Africa and are also cultivated in the U.S., India, Pakistan and northern China. Johnson grass is heat resistant and well adapted to warm conditions. The pollen of Johnson grass, Bahia and Bermuda grass constitute the allergenically important grass pollens in the southern United States (French and Major, *J. Allergy* 1:286–291 (1930); Martin et al., *Ann. Allergy* 54:992–104 (1985)). Both Johnson grass and Bahia are members of the subfamily Panicoideae, which also includes the economically important genera Saccharum (sugar cane) and Zea (maize) (Watson, 1990, *Reproductive Versatility in the Grasses* (G. P. Chapman ed.) Cambridge University Press, pp. 258–265)).

The allergenic importance of Johnson grass in areas where it has wide distribution has been reported in the literature (French and Major, 1930, supra). It appears to share allergenicity with both Bermuda grass from subfamily Chlorideae, and the temperate grasses of subfamily Pooideae (Martin et al., 1985, supra). The Group I allergen of Johnson grass has been shown to have antigenic cross-reactivity with other Group I allergens (Singh and Knox, *Int. Arch. All. App. Immunol.* 72:243–248 (1985)).

Treatment of sensitivity to grass pollen allergens by administration of pollen extract to effect hyposensitization to the allergen has been attempted. Hyposensitization using pollen extract, however, has drawbacks in that it can elicit anaphylaxis if high doses are used, whereas when low doses are used to avoid anaphylaxis, treatment must be continued for several years to build up a tolerance for the extract. Despite the attention grass pollen allergens have received, definition or characterization of the Johnson grass pollen allergens responsible for its adverse effects on people is far from complete.

SUMMARY OF THE INVENTION

The present invention provides nucleic acid sequences coding for Sor h I, the major pollen allergen of *Sorghum halepense*, and fragments thereof. The present invention also provides isolated Sor h I protein or at least one fragment thereof produced in a host cell transformed with a nucleic acid having a nucleotide sequence coding for Sor h I or at least one fragment thereof, and isolated fragments of Sor h I prepared synthetically. As used herein, a fragment of the nucleic acid sequence coding for the entire amino acid sequence of Sor h I refers to a nucleotide sequence having fewer bases than the nucleotide sequence coding for the entire amino acid sequence of Sor h I and/or mature Sor h I. Such protein, and fragments thereof, are useful for diagnosing, treating, and preventing sensitivity to Johnson grass pollen allergens. This invention is more particularly described in the appended claims and is described in its preferred embodiments in the following description.

BRIEF DESCRIPTION OF THE DRAWINGS

FIG. 5 is the nucleotide sequence (SEQ ID NO: 1) and the deduced amino acid sequence (SEQ ID NO: 2) of Sor h I clone 3S.

FIG. 7 is a comparison of the nucleotide sequences of rye grass allergen Lol p I (SEQ ID NO: 3) and Johnson grass allergen Sor h I (SEQ ID NO: 1). The dots in the Sor h I sequence represent homology with Lol p I.

FIG. 8 is a comparison of the deduced amino acid sequences of Lol p I (SEQ ID NO: 4) and Sor h I (SEQ ID NO: 2). Identical residues are shown by colons. The similar residues are indicated by "s".

DETAILED DESCRIPTION OF THE INVENTION

Figure 1E:
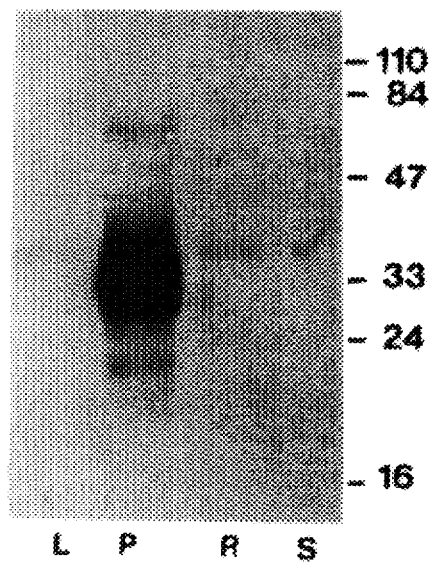
FIG. 1 shows immunoblot analysis of Johnson grass pollen proteins from different tissues. Panel A: protein profiles revealed by Coomassie Brilliant Blue R250 staining. Panel B: antibodies from pooled sera of grass pollen allergic individuals. Panel C: mAb FMC-A1. Panel D: mAb CdI-1D1, Panel E: mAb CdI-3A2 and Panel F: mAb CdI-4D2.

The present invention provides nucleic acid sequences coding for Sor h I, a major allergen found in Johnson grass pollen. The nucleic acid sequence coding for Sor h I preferably has the sequence shown in FIG. 5 (SEQ ID NO: 1). Sequence analysis of the Sor h I clone 3S revealed that the cDNA insert is 1072 nucleotide long and contains 3 possible in-frame ATG start codons at nucleotide positions 25, 37 and 40. The ATG codon at position 40 is proposed as the site for translation initiation. This corresponds to an open reading frame of 783 nucleotides terminating with a TAA stop codon at position 823 and coding for a protein of 261 amino acids. See FIG. 5 (SEQ ID NO: 1 and 2). A host cell transformed with a vector containing the cDNA insert of clone 3S has been deposited with the American Type Culture Collection ATCC No. 69106 deposited Oct. 28, 1992.

The predicted amino acid sequence of Sor h I clone 3S has a putative signal peptide sequence of 23 amino acids. This signal peptide is hydrophobic and contains small chain amino acids in positions −1 and −3 relative to the peptide cleavage site. Thus, the mature processed Sor h I protein is 238 amino acids with a calculated molecular mass of 25.8 kD. There is one possible asparagine-linked glycosylation site at the asparagine residue at position 9 (FIG. 5), in the hydrophilic region of the protein, which conforms to the consensus sequence Asn-X-Ser/Thr. Utilization of this glycosylation site will increase the molecular weight and affect the pI of the mature protein.

The sequence of an additional Sor h I clone, clone 2S corresponds to 451 nucleotides between positions 594 and 945 in the clone 3S sequence. It is expected that there are nucleotide sequence polymorphisms in Sor h I, and it will be appreciated by one skilled in the art that one or more nucleotides (up to about 1% of the nucleotides) in the nucleic acid sequence coding for Sor h I may vary among individual *Sorghum halepense* plants due to natural allelic variation. Any and all such nucleotide variations and resulting amino acid polymorphisms are within the scope of the invention. Furthermore, there may be one or more family members of Sor h I. Such family members are defined as proteins related in function and amino acid sequence to Sor h I but encoded by genes at separate genetic loci.

The Group I allergen of Johnson grass, Sor h I is similar to Lol p I, a major allergen of rye-grass pollen, in many aspects. Sor h I has a molecular mass around 35 kD and antigenic cross-reactivity with anti-Lol p I and anti-Cyn d I (a major allergen of Bermuda grass) monoclonal antibodies. Similar to Lol p I, Sor h I shows tissue specific expression and is detected only in pollen. It shares extensive homology with Lol p I in terms of both nucleotide and amino acid sequence (see FIG. 7, SEQ ID NO: 3 and FIG. 8, SEQ ID NO: 4).

Comparison of the region identified as the allergenically important site in Group I allergens of five grasses (i.e., Lol p I (SEQ ID NO: 8), Fes e I (SEQ ID NO: 9), Agr a I (SEQ ID NO: 10), Poa p I (SEQ ID NO: 11) and Ant o I (SEQ ID NO: 12)) with the corresponding sequence in Johnson grass (SEQ ID NO: 13) reveals that Sor h I is also highly conserved in this region (see Table IV). Although there is a difference of 6 amino acids in this region, 3 of these are conservative. It is of interest to note that differences were observed between Lol p I and the other 4 grasses studied in positions 7, 9, 11, 21 and 26 (Esch and Klapper, *Mol. Immunol.* 26:557–561 (1989)). Three of these positions, 9, 11 and 26 coincide with those where differences were observed in Sor h I. In fact, in one of the isoforms of Lol p I, Phe replaces the Val residue at position 11 (Perez et al. (1990) *J. Biol. Chem.* 265:16210–16215). This may suggest that these residues are not as important in terms of epitope structure. Alternatively, lysine, which may be involved in epitope structure is conserved among the five grasses and one of these residues at position 8 falls within a putative antigenic determinant predicted by a Hopp and Woods, (1983) hydrophilicity index plot (Esch and Klapper, supra, 1989).

There was no concordance in the patterns of IgE binding from grass allergic patients' sera between Sor h I and Lol p I, despite the extensive homology observed in the region described as the allergenic determinant in terms of IgE binding for Lol p I. One possible explanation for this is that separate exposure is required for sensitization to Sor h I. A similar conclusion was reported for Bermuda grass by Schumacher et al., (*Ann. Allergy,* 55:584–587 (1985)), who reported that patients sensitized to Bermuda grass do not possess IgE antibodies that show significant reactivity with other grass pollen allergens. In the case of patients with IgE antibodies to several grasses, including Bermuda grass, sensitivities to the non-Bermuda grasses require exposure to at least one of them. This is in contrast to the observations of Matthiesen and Lowenstein, (*Clin. Exp. Allergy* 21:309–320 (1991)), who found IgE antibodies against Bermuda grass in Danish grass pollen allergic patients, although Bermuda grass is, not found in Denmark.

Fragments of the nucleic acid sequence coding for protein fragments of Sor h I are within the scope of the invention. Fragments within the scope of the invention include those coding for fragments of Sor h I which induce an immune response in mammals, preferably humans, such as stimulation of minimal amounts of IgE; binding of IgE; eliciting the production of IgG and IgM antibodies; or the eliciting of a T cell response such as proliferation and/or lymphokine secretion and/or the induction of T cell energy. The foregoing fragments of Sor h I are referred to herein as antigenic fragments. Nucleic acid fragments within the scope of the invention also include those capable of hybridizing with nucleic acid from other plant species for use in screening protocols to detect allergens that are cross-reactive with Sor h I. As used herein, a fragment of the nucleic acid sequence coding for Sor h I refers to nucleotide sequence having fewer bases than the nucleotide sequence coding for the entire amino acid sequence of Sor h I and/or mature Sor h I. Generally, the nucleic acid sequence coding for the fragment or fragments of Sor h I will be selected from the bases coding for the mature protein, however, in some instances it may be desirable to select all or a part of a fragment or fragments from the leader sequence portion of the nucleic acid sequence of the invention. Such nucleic acid sequences may also contain linker sequences, modified restriction endonuclease sites and other sequences useful for cloning, expression or purification of Sor h I or fragments thereof.

A nucleic acid sequence coding for Sor h I may be obtained from *Sorghum halepense* plants. It may also be possible to obtain the nucleic acid sequence coding for Sor h I from genomic DNA. *Sorghum halepense* is a well-known species of cereal grain, and plant material may be obtained from wild, cultivated, or ornamental plants. The nucleic acid sequence coding for Sor h I can be obtained using the method disclosed herein or any other suitable techniques for isolation and cloning of genes. The nucleic acid sequences of the invention may be DNA or RNA.

The present invention provides expression vectors and host cells transformed to express the nucleic acid sequences of the invention. A nucleic acid sequence coding for Sor h I, or at least one fragment thereof, can be expressed in bacterial cells such as *E. coli*, insect cells (baculovirus), yeast, or mammalian cells such as Chinese hamster ovary cells (CHO). Suitable expression vectors, promoters, enhancers, and other expression control elements can be found in Sambrook et al., *Molecular Cloning: A Laboratory Manual*, second edition, Cold Spring Harbor Laboratory Press, Cold Spring Harbor, N.Y. (1989). Other suitable expression vectors, promoters, enhancers, and other expression elements are known to those skilled in the art. Expression in mammalian, yeast or insect cells leads to partial or complete glycosylation of the recombinant material and formation of any inter- or intra-chain disulfide bonds. Suitable vectors for expression in yeast include YepSecl (Baldari et al. (1987) *Embo J.* 6:229–234); pMFa (Kurjan and Herskowitz (1982) *Cell* 30:933–943); JRY88 (Schultz et al. (1987) *Gene* 54:113–123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commercially available (Pharmacia, Piscataway, N.J.) for expression in mammalian cells.

For expression in *E. coli*, suitable expression vectors include, among others, pTRC (Amann et al. (1988) *Gene* 69:301–315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol* 64:3963–3966; and pSEM (Knapp et al. (1990) BioTechniques 8:280–281). The use of pTRC, and pET-11d, for example, will lead to the expression of unfused protein. The use of pMAL, pRIT5 pSEM and pGEX will lead to the expression of allergen fused to maltose E binding protein (pMAL), protein A (pRIT5), truncated β-galactosidase (PSEM), or glutathione S-transferase (pGEX).

When Sor h I, a fragment, or fragments thereof is expressed as a fusion protein, it is particularly advantageous to introduce an enzymatic cleavage site at the fusion junction between the carrier protein and Sor h I, or fragment thereof. Sor h I or fragment thereof can then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass.

Suitable vectors may have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant Sor h I in different *E. coli* hosts that have an altered capacity to degrade recombinantly expressed proteins (e.g., U.S. Pat. No. 4,758,512). Alternatively, it may be advantageous to alter the nucleic acid sequence to use codons preferentially utilized by *E. coli*, where such nucleic acid alteration would not affect the amino acid sequence of the expressed protein.

Host cells can be transformed to express the nucleic acid sequences of the invention using conventional techniques such as calcium phosphate or calcium chloride co-precipitation, DEAE-dextran-mediated transfection, or electropotation. Suitable methods for transforming the host cells can be found in Sambrook et al. supra, and other laboratory textbooks.

The nucleic acid sequences of the invention can also be chemically synthesized using standard techniques.

The present invention also provides a method of producing isolated Sor h I protein, or at least one isolated fragment thereof. A host cell transformed with a DNA sequence encoding Sor h I or fragment thereof, is cultured in an appropriate medium to produce a mixture of cells and medium containing Sor h I protein, or fragment thereof. The mixture is purified to produce substantially pure Sor h I protein, or at least one fragment thereof. Suitable mediums for cell culture are well known in the art. Sor h I protein and peptides can be purified from cell culture medium, host cells, or both using techniques known in the art for purifying peptides and proteins including ion-exchange chromatography, gel filtration chromatography, ultrafiltration, electrophoresis and immunopurification with antibodies specific for Sor h I or fragments thereof. The terms isolated and purified are used interchangeably herein and refer to peptides, protein, protein fragments, and nucleic acid sequences substantially free of cellular material or culture medium when produced by recombinant DNA techniques, or chemical precursors or other chemicals when synthesized chemically.

Fragments of an allergen from Johnson grass pollen, eliciting a desired antigenic response (referred to herein as antigenic fragments) may be obtained, for example, by screening peptides recombinantly produced from the corresponding fragment of the nucleic acid sequence of Sor h I coding for such peptides. In addition, fragments can be chemically synthesized using techniques known in the art. For example, the allergen may be arbitrarily divided into fragments of a desired length, with no overlap of the fragments, or preferably divided into overlapping fragments of a desired length. The fragments are tested to determine their antigenicity (e.g., the ability of the fragment to induce an immune response in a mammal). If fragments of Sor h I are to be used for therapeutic purposes, then the fragments which are capable of eliciting a T cell response, such as stimulation (i.e., proliferation or lymphokine secretion) and/or are capable of inducing T cell anergy are particularly desirable.

Fragments of Sor h I which have minimal IgE stimulating activity are also desirable. Minimal IgE stimulating activity refers to IgE stimulating activity which is less than the amount of IgE production stimulated by purified, native Sor h I protein. Additionally, for therapeutic purposes, isolated Sor h I, and fragments thereof, preferably do not bind IgE specific for Johnson grass or bind such IgE to a substantially lesser extent than the purified native Johnson grass allergen binds such IgE. If the isolated Sor h I or fragment thereof binds IgE, it is preferable that such binding does not result in the release of mediators (e.g., histamines) from mast cells or basophils.

Isolated Sor h I, or preferred antigenic fragments thereof, when administered to an individual sensitive to Johnson grass pollen, are capable of modifying the allergic response of the individual to Johnson grass pollen. Additionally, isolated Sor h I, or preferred antigenic fragments can be administered to an individual allergic to an allergen cross-reactive with a Johnson grass allergen, such as an allergen from the pollen of *Lolium perenne* or *Cynodon dactylon* to modify the allergic response of the individual to such cross-reactive allergen. Preferably, administration of isolated Sor h I or an antigenic fragment thereof to an individual modifies the B-cell response, T-cell response or both the B-cell and the T-cell response of the individual to the allergen. As used herein, modification of the allergic response of an individual sensitive to a Johnson grass pollen allergen can be defined as non-responsiveness or diminution in symptoms to the allergen, as determined by standard clinical procedures (See e.g., Varney et al., *British Medical Journal*, 302:265-269 (1990)), including diminution in Johnson grass pollen induced asthmatic symptoms. As referred to herein, a diminution in symptoms includes any reduction in the allergic response of an individual to the allergen following a treatment regimen with a peptide or protein of the invention. This diminution in symptoms may be determined subjectively (i.e., the patient feels more comfortable upon exposure to the allergen), or clinically such as with a standard skin test.

The isolated Sor h I protein or isolated fragments thereof are preferably tested to determine therapeutic effectiveness in appropriate mammalian models such as the mouse model disclosed in Tamura et al. (1986) *Microbiol. Immunol.* 30:883-896 and U.S. Pat. No. 4,939,239, or the primate model disclosed in Chiba et al. (1990) *Int. Arch. Allergy Immunol.* 93:83-88. Initial screening for IgE binding to Sor h I protein or fragments thereof may be performed by scratch tests or intradermal skin tests on laboratory animals or human volunteers, or in in vitro systems such as RAST (radioallergosorbent test), RAST inhibition, ELISA assay, radioimmunoassay (RIA), or histamine release.

Isolated antigenic fragments or peptides which have T cell stimulating activity, and thus comprise at least one T cell epitope of Sor h I are particularly desirable. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T cell epitope is the basic element or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Exposure of allergic individuals to isolated Sor h I or an isolated peptide which comprises at least one T cell epitope of Sor h I, may tolerize or anergize appropriate T cell subpopulations such that they become unresponsive to the protein allergen and do not participate in stimulating an immune response upon such exposure. In addition, administration of the protein allergen of the invention or peptide which comprises at least one T cell epitope may modify the lymphokine secretion profile as compared with exposure to the naturally-occurring protein allergen or portion thereof (e.g., result in a decrease of IL-4 and/or an increase in IL-2). Furthermore, exposure to such peptide or protein allergen may influence T cell subpopulations which normally participate in the response to the allergen such that these T cells are drawn away from the site(s) of normal exposure to the allergen (e.g., nasal mucosa, skin, and lung) towards the site(s) of therapeutic administration of the fragment or protein allergen. This redistribution of T cell subpopulations may ameliorate or reduce the ability of an individual's immune system to stimulate the usual immune response at the site of normal exposure to the allergen, resulting in a diminution in allergic symptoms.

The isolated Sor h I protein and isolated fragments or portions derived therefrom (peptides) can be used in methods of diagnosing, treating and preventing allergic reactions to Johnson grass pollen allergens or an immunologically cross-reactive protein allergen. Thus, the present invention provides therapeutic compositions comprising isolated Sor h I, or at least one fragment thereof, produced in a host cell transformed to express Sor h I or at least one fragment thereof, and a pharmaceutically acceptable carrier or diluent. The therapeutic compositions of the invention may also comprise isolated Sor h I protein or at least one isolated fragment thereof produced by chemical synthesis.

Administration of the therapeutic compositions of the present invention to an individual to be desensitized can be carried out using known techniques. Sor h I protein, or at least one isolated fragment thereof, can be administered to an individual in combination with, for example, an appropriate diluent, a carrier and/or an adjuvant. Pharmaceutically acceptable diluents include saline and aqueous buffer solutions. Pharmaceutically acceptable carriers include polyethylene glycol (Wie et al. (1981) *Int. Arch. Allergy Appl. Immunol.* 64:84-99) and liposomes (Strejan et al. (1984) *J. Neuroimmunol.* 7:27). For purposes of inducing T cell anergy, the therapeutic composition is preferably administered in nonimmunogenic form, e.g., it does not contain adjuvant. Such compositions will generally be administered by injection (subcutaneous, intravenous, etc.), oral administration, inhalation, transdermal application or rectal administration.

The therapeutic compositions of the invention are administered to individuals sensitive to Johnson grass pollen at dosages and for lengths of time effective to reduce sensitivity (i.e., reduce the allergic response) of the individual to Johnson grass pollen. Effective amounts of the therapeutic compositions will vary according to factors such as the degree of sensitivity of the individual to Johnson grass, the age, sex, and weight of the individual, and the ability of the Sor h I protein or fragment thereof to elicit an antigenic response in the individual.

The Sor h I cDNA (or the mRNA from which it was transcribed) or a portion thereof may be used to identify similar sequences in any variety or type of plant and thus, to identify or "pull out" sequences which have sufficient homology to hybridize to the Sor h I cDNA or mRNA or portion thereof, under conditions of low stringency. Those sequences which have sufficient homology (generally greater than 40%) may be selected for further assessment using the method described herein. Alternatively, high stringency conditions may be used. In this manner, DNA of the present invention may be used to identify, in other types of plants, preferably related families, genera, or species, sequences encoding polypeptides having amino acid sequences similar to that of Sor h I and, thus, to identify allergens in other species.

Isolated allergenic proteins, or fragments thereof, that are immunologically related to Sor h I, such as by antibody cross-reactivity or T-cell cross-reactivity, other than those already identified, are within the scope of the invention. Such proteins or fragments thereof bind antibodies specific for the protein and peptides of the invention or stimulate T cells specific for the protein and peptides of this invention.

Proteins or peptides encoded by the cDNA of the present invention can be used, for example as "purified" allergens. Such purified allergens are useful in the standardization of allergen extracts which are key reagents for the diagnosis and treatment of allergy to Johnson grass. Furthermore, by using peptides based on the nucleic acid sequence of Sor h I, anti-peptide antisera or monoclonal antibodies can be made using standard methods. These sera or monoclonal antibodies can be used to standardize allergen extracts.

Through use of the peptides and protein of the present invention, preparations of consistent, well-defined composition and biological activity can be made and administered for therapeutic purposes (e.g., to modify the allergic response of an individual sensitive to Johnson grass). Administration of such peptides or protein may, for example, modify B-cell response to Sor h I allergen, T-cell response to Sor h I allergen or both responses. Isolated peptides can also be used to study the mechanism of immunotherapy of allergy to Johnson grass pollen and to design modified derivatives or analogues useful in immunotherapy.

Work by others has shown that high doses of allergens generally produce the best results (i.e., greatest symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a protein or peptide of the present invention (e.g., one having all or a portion of the amino acid sequence of Sor h I), or a modified protein or peptide, or protein or peptide analogue.

It is possible to modify the structure of a protein or peptide of the invention for such purposes as increasing solubility, enhancing therapeutic or preventive efficacy, or stability (e.g., shelf life ex vivo, and resistance to proteolytic degradation in vivo). A modified protein or peptide can be produced in which the amino acid sequence has been altered, such as by amino acid substitution, deletion, or addition, to modify immunogenicity and/or reduce allergenicity, or to which a component has been added for the same purpose. For example, the amino acid residues essential to T cell epitope function can be determined using known techniques (e.g., substitution of each residue and determination of the presence or absence of T cell reactivity). Those residues shown to be essential can be modified (e.g., replaced by another amino acid whose presence is shown to enhance T cell reactivity), as can those which are not required for T cell reactivity (e.g., by being replaced by another amino acid whose incorporation enhances T cell reactivity but does not diminish binding to relevant MHC). Another example of a modification of protein or peptides is substitution of cysteine residues preferably with alanine, serine, threonine, leucine or glutamic acid to minimize dimerization via disulfide linkages. Peptides of the invention can also be modified by chemical modification of amino acid side chains or cyclization of the peptide.

In order to enhance stability and/or reactivity, the protein or peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention. Furthermore, proteins or peptides of the present invention can be modified using the polyethylene glycol (PEG) method of A. Sehon and co-workers (Wie et al. supra) to produce a protein or peptide conjugated with PEG. In addition, PEG can be added during chemical synthesis of a protein or peptide of the invention. Modifications of proteins or peptides or portions thereof can also include reduction/alkylation (Tarr in: *Method of Protein Microcharacterization*, J. E. Silver ed. Humana Press, Clifton, N.J., pp. 155–194 (1986)); acylation (Tarr, supra); chemical coupling to an appropriate carrier (Mishell and Shiigi, eds, *Selected Method in Cellular Immuology*, W. H. Freeman, San Francisco, Calif. (1980); U.S. Pat. No. 4,939, 239; or mild formalin treatment (Marsh *International Archives of Allergy and Applied Immunology*, 41:199–215 (1971)).

To facilitate purification and potentially increase solubility of proteins or peptides of the invention, it is possible to add reporter group(s) to the peptide backbone. For example, poly-histidine can be added to a peptide to purify the peptide on immobilized metal ion affinity chromatography (Hochuli, E. et al., *Bio/Technology*, 6:1321–1325 (1988)). In addition, specific endoprotease cleavage sites can be introduced, if desired, between a reporter group and amino acid sequences of a peptide to facilitate isolation of peptides free of irrelevant sequences. In order to successfully desensitize an individual to a protein antigen, it may be necessary to increase the solubility of a protein or peptide by adding functional groups to the peptide or by not including hydrophobic regions such as hydrophobic T cell epitopes.

To potentially aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during recombinant construction of the peptide. The resulting peptide can be rendered sensitive to cathepsin and/or other trypsin-like enzymes cleavage to generate portions of the peptide containing one or more T cell epitopes. In addition, such charged amino acid residues can result in an increase in solubility of a peptide.

Site-directed mutagenesis of DNA encoding a peptide or protein of the invention (e.g., Sor h I or a fragment thereof) can be used to modify the structure of the peptide or protein by methods known in the art. Such methods may, among others, include PCR with degenerate oligonucleotides (Ho et al., *Gene*, 77:51–59 (1989)) or total synthesis of mutated genes (Hostomsky, Z. et al., *Biochem. Biophys. Res. Comm.* 161:1056–1063 (1989)). To enhance bacterial expression, the aforementioned methods can be used in conjunction with other procedures to change the eukaryotic codons in DNA constructs encoding protein or peptides of the invention to ones preferentially used in *E. coli*, yeast, mammalian cells, or other eukaryotic cells.

Using the structural information now available, it is possible to design Sor h I peptides which, when administered to an individual sensitive to Johnson grass, in sufficient quantities, will modify the individual's allergic response to a Johnson grass pollen allergen. This can be done, for example, by examining the structure of Sor h I, producing peptides (via an expression system, synthetically or otherwise) to be examined for their ability to influence B-cell and/or T-cell responses in sensitive individuals and selecting appropriate peptides which contain epitopes recognized by the cells. In referring to an epitope, the epitope will be the basic element or smallest unit of recognition by a receptor, particularly immunoglobulins, histocompatibility antigens and T cell receptors where the epitope comprises amino acids essential to receptor recognition. Amino acid sequences which mimic those of the epitopes and which are capable of down regulating allergic response to Sor h I can also be used.

It is now also possible to design an agent or a drug capable of blocking or inhibiting the ability of Sor h I to induce an allergic reaction in sensitive individuals. Such agents could be designed, for example, in such a manner that they would bind to relevant anti-Sor h I IgEs, thus preventing IgE-allergen binding and subsequent mast cell degranulation. Alternatively, such agents could bind to cellular components of the immune system, resulting in suppression or desensitization of the allergic response to Johnson grass pollen allergens. A non-restrictive example of this is the use of appropriate B- and T-cell epitope peptides, or modifications thereof, based on the cDNA/protein structures of the present invention to suppress the allergic response to Johnson grass pollen. This can be carried out by defining the structures of B- and T-cell epitope peptides which affect B- and T-cell function in in vitro studies with blood components from Johnson grass pollen sensitive individuals.

Protein, peptides or antibodies of the present invention can also be used for detecting and diagnosing sensitivity to Johnson grass allergens. For example, this could be done by combining blood or blood products obtained from an individual to be assessed for sensitivity with an isolated antigenic peptide or peptides of Sor h I, or isolated Sor h I protein, under conditions appropriate for binding of components in the blood (e.g., antibodies, T-cells, B-cells) with the peptide(s) or protein and determining the extent to which such binding occurs. Other diagnostic methods for allergic diseases which the protein, peptides or antibodies of the present invention can be used include radio-allergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The DNA used in any embodiment of this invention can be cDNA obtained as described herein, or alternatively, can be any oligodeoxynucleotide sequence having all or a portion of a sequence represented herein, or their functional equivalents. Such oligodeoxynucleotide sequences can be produced chemically or enzymatically, using known techniques. A functional equivalent of an oligonucleotide sequence is one which is 1) a sequence capable of hybridizing to a complementary oligonucleotide to which the sequence (or corresponding sequence portions) of FIG. 5, SEQ ID NO: 1, or fragments thereof hybridizes, or 2) the sequence (or corresponding sequence portion) complementary to FIG. 5, SEQ ID NO: 1, and/or 3) a sequence which encodes a product (e.g., a polypeptide or peptide) having the same functional characteristics of the product encoded by the sequence (or corresponding sequence portion) of FIG. 5, SEQ ID NO: 1. Whether a functional equivalent must meet one or both criteria will depend on its use (e.g., if it is to be used only as an oligoprobe, it need meet only the first or second criteria and if it is to be used to produce Sor h I protein, it need only meet the third criterion).

This invention is further illustrated by the following non-limiting examples.

EXAMPLES

A. MATERIALS

1. Plant Material

Seeds of Johnson grass, *Sorghum halepense*, were kindly supplied by Mr. P. Taylor, School of Botany, University of Melbourne. The seeds were planted and grown in a glasshouse. Anthers were collected from newly flowering spikes using fine forceps.

Vegetative tissues such as leaves and roots were obtained by germinating the seeds on moist filter paper (Whatman 3 mm, Whatman Inc., Clifton, N.J.) and growing them for 2–3 weeks, until the seedling were 6–7 cm tall. The roots and leaves were removed using fine forceps, placed into plastic tubes and frozen in liquid nitrogen. They were stored in liquid nitrogen till required.

Dry stored pollens of Johnson grass studied during the course of this work were purchased from Greet Laboratories (Lenoir, N.C., U.S.A.), Hollister-Steir (Spokane, Wash., U.S.A.) and Biopol Laboratories (Spokane Wash., U.S.A.).

2. Commercially available materials

The messenger RNA purification kit, You-prime cDNA synthesis kit, T7 polymerase sequencing kit Deeaza T7 polymerase kit, Gene Ataq sequencing kit and the deoxynucleotides (dNTPs) were purchased from Pharmacia (Upsalia, Sweden). The oligo-labelling kit was from Bresatec (SA, Australia). Glutagene Glutathione S-transferase cloning and sequencing kit was purchased from Amrad Corporation Ltd, (VIC, Australia). Mouse monoclonal isotyping kit and the intense BL silver enhancement kit were from Amersham International (UK). The λ gt11 and Packagene extract system, pGEM-4Z plasmid system, promoter primers Sp6, T7 and T3 were purchased from Promega Corporation (Madison, Wis., U.S.A.). Sequagel sequencing system was purchased from National Diagnostics (Manville, N.J., U.S.A.).

All restriction enzymes were purchased from Promega and Pharmacia and used under the conditions recommended by the manufacturer. The materials and chemicals used in oligonucleotide synthesis were from Pharmacia (Upsalla, Sweden). Agarose was from Promega and low melting agarose was from Bethesda Research Laboratories (Gaithersburg, Md., U.S.A.).

3. Monoclonal antibodies

Some of the monoclonal antibodies used in this study were kindly made available by other researchers. FMC-A1 (40.1) and FMC-A7 (12.3) were provided by Dr. I. Smart, Flinders Medical Centre, (Adelaide SA, Australia). New data indicated that the original FMC-A1 preparation may be polyclononal rather than monoclonal. One antibody in the FMC-A1 preparation appeared to be specific for Lol p Ia, while a second antibody appeared to be specific for Lol p Ib, which may indicate polyclonality in this antibody preparation. The antibodies 21.3 and 3.2 against rye-grass Group I allergens, were provided by Dr. D. G. Marsh, Johns Hopkins Asthma and Allergy Centre (Baltimore, Md., U.S.A.). The antibodies LpIX-3A and LpIX-4A were produced as described in section 13 below. The monoclonals CdI-1D1, CdI-3A2 and CdI-4D2 were raised against the Group I allergen of Bermuda grass *Cynodon dactylon* and made available by Miss P. M. Smith (University of Melbourne, Melbourne, Australia). The mAb against chicken thymus was provided by Dr. John Pettit, Alfred Hospital (Melbourne, VIC Australia).

The horse radish peroxidase (HRP) conjugated sheep antimouse antibody was purchased from Silenus (Melbourne, VIC, Australia) and the HRP-goat anti-rabbit antibody was from Promega. The rabbit antihuman IgE antibody was purchased from Dakopatts Corporation (Carpinteria, Calif., U.S.A.) and the $^{125}$I-labeled goat anti-human IgE was from Kallestad Laboratories (Chaska, Minn., U.S.A.).

4. Human serum

The sera were donated by allergic and non-allergic individuals and collected, after informed consent, by medical practitioners. The allergic individuals showed typical symptoms of seasonal hay fever and asthma during the grass pollen season and gave a positive response to skin prick tests with grass pollen extract. The sera were assayed for IgE reactivity with soluble proteins of rye-grass pollen on Western blots.

B. METHODS

1. Protein isolation

Soluble proteins were extracted from the grass pollen by vigorous shaking in phosphate buffered saline (PBS; 150 mM NaCl, 16 mM $Na_2HPO_4$, 4 mM $NaHPO_4$, pH 7.2) containing 1 mM phenylmethylsulfonyl fluoride (PMSF) on ice for 3 hours. The solution was cleared by centrifugation at 2500 rpm at 4° C. for 20 minutes and the supernatant collected. Protein concentration was determined using the Bio-Rad (Richmond, Calif., U.S.A.) micro protein assay and bovine gamma globulin standards. The proteins were aliquoted and stored at −20° C.

The vegetative tissues (leaf, roots and seeds) were collected and immediately frozen in liquid nitrogen. They were ground to a fine powder using a mortar and pestle, while still frozen. The proteins were extracted by adding PBS containing 1 mM PMSF and shaking on ice for 1 hour. The supernatants were clarified by centrifugation at 2500 rpm. The samples were stored at −20° C. after the protein concentration was determined as described above.

2. SDS-PAGE

Sodium dodecyl sulphate polyacrylamide gel electrophoresis (SDS-PAGE) was performed using a resolving gel, a 4% stacking gel and the Laemmli buffer system (Laemmli, *Nature* 227:680, 1970). The gels were calibrated using either low molecular weight markers (Pharmacia, Upsalla, Sweden) or Bio-Rad (Richmond, Calif.) pre-stained low molecular weight markers. Samples for electrophoresis were diluted 1:1 in SDS/reducing sample buffer (62 mM Tris pH6.8, 0.2% SDS, 50 mM DTT, 10% glycerol and bromophenol blue) and boiled for 5 minutes prior to loading.

When a gradient SDS-PAGE was conducted, a 10–15% resolving gradient gel was cast utilizing a peristaltic pump and a Bio-Rad (Richmond, Calif.) Protean II slab gel apparatus. The gels were 140 mm×115 mm and 1.5 mm in thickness. The gels were loaded with appropriate amount of protein and run at constant current, 20 mA/gel for 1 hour then 30 mA/gel until the dye front was approximately 1 cm from the end of the gel.

When 12% resolving minigels were conducted, they were cast utilising a Bio-Rad Mini-Protean II apparatus. The gel dimensions were 80 mm×73 mm×1 mm. Electrophoresis was performed at constant voltage of 200V per gel for approximately 1 hour.

The proteins separated by SDS-PAGE were visualized by Coomassie brilliant blue R250 staining (0.2% weight for volume Coomassie brilliant blue R250, 50% methanol, 10% glacial acetic acid) for 1 hour then desrained in a solution containing 10% acetic acid, 5% methanol and 3% glycerol.

3. Western blotting

Proteins separated by SDS-PAGE were electrophoretically transferred from the gel onto nitrocellulose membrane (0.45 µm, Schleicher and Schuell, Dassel, Germany) according to the procedure of Towbin et al., (*Proc. Natl. Acad. Sci USA* 76:4350–4354 (1979)) in a Bio-Rad transblot cell containing transblot buffer (20 mM Tris, 150 mM glycine, 20% methanol).

The transfer conditions for gradient gels were constant voltage of 150 mA overnight at 4° C. and for the minigels constant current of 200 mA for 2–3 hours at room temperature.

4. Slot immunoblotting

For slot immunoblots, 100 µl sample containing 2 µg of total pollen protein was applied to the nitrocellulose membrane using a Minifold II slot blotting apparatus (Schleicher and Schuell, Keene, N.H.). This was washed in PBS and blocked in the same buffer containing 10% low fat milk powder and screened as described below.

5. Immunological screening of proteins

The following procedures were used for the immunological screening of any protein immobilized on a nitrocellulose membrane. This included Western blots, protein plaque lifts and protein dot blots.

(i) Screening with monoclonal antibodies

The nitrocellulose membrane was incubated in 10% nonfat milk powder in PBS for 1 hour in order to block additional protein binding sites. The membrane was then washed four times in PBS, placed in appropriate antibody solution diluted in PBS containing 0.5% bovine serum albumin (BSA). The membrane was incubated at room temperature for 1–2 hours. The membrane was washed, once in PBS with 0.1% Tween 20 (TPBS) and twice in PBS, and incubated in appropriate HRP conjugated second antibody for 1 hour. The second antibody was either HRP anti-mouse (Silenus, Melbourne, VIC, Australia), diluted 1:500 in PBS-0.5% BSA or HRP anti-rabbit (Promega, Madison, Wis.), 1:2500 dilution in PBS-0.5% BSA. The membrane was washed twice in TPBS, twice in PBS and the colour developed at 37° C. by adding peroxidase substrate 4-Chloro-1-naphthol (Sigma Chemical Co., St. Louis, Mo., U.S.A.).

(ii) Affinity purification of IgE antibodies

Affinity purified IgE antibodies reactive with purified cDNA clones of Johnson grass obtained as described in Sections 6–12 were obtained. The cDNA clones in X were densely plated out and fusion protein production induced by overlaying the plates with isopropyl-β-D-thiogalactopyranoside (IPTG) impregnated nitrocellulose membranes (0.45 µm, Schleicher and Schuell, Keene, N.H.). The membranes containing the recombinant protein, were then blocked in 10% milk powder, washed and incubated overnight in pooled allergic sere, which had already been incubated with *E. coli* extract. The membranes were washed twice in TPBS and then with PBS only. The bound IgE antibodies were eluted with 0.1M glycine hydrochloride, pH 2.6, containing 1% BSA. The purified antibodies were used to probe Western blots. Binding of the IgE was visualized using $^{125}$I-labelled goat anti-human IgE followed by autoradiography as described in the previous section.

6. Isolation of total RNA

The procedure used for the isolation of total RNA from Johnson grass was a modified version of the guenidinium isothiocyanate method of Chomczynski and Sacchi (*Anal. Biochem* 162:156–159 (1987)). Fresh or stored tissues from pollen, leaves, roots or other plant tissues were ground to a fine powder in liquid nitrogen in the presence of 5M quanidinium isothiocyanate (Fluke, FRG) in 0.05M Tris-HCl pH 7.0, 0.05 volume of pure β-mercaptoethenol (2ME Kochlight Ltd.) and 0.1 volumes of 5% Sarcosyl. The slurry was centrifuged at 7000×g for 30 minutes, supernatants decanted into polyallomer Beckman quick-seal ultracentrifuge tubes (Beckman, Palo Alto, Calif., U.S.A.) (16×76 mm) underlaid with a 3 ml CsCl cushion (5.7M CsCl in 0.1M EDTA; density=1.71 g/ml). After centrifugation in a Ti 70.1 rotor in a Beckman L8-70 ultracentrifuge at 40,000 rpm for 20 hours at 20° C., supernatants were aspirated to the cushion interface and the tubes inverted. The RNA pellets were air dried briefly, resuspended in 0.05% SDS then extracted with an equal volume of phenol to remove contaminating proteins. The RNA was then precipitated with 0.1 volumes of 3M sodium acetate and 2.5 volumes 100% ethanol overnight at −70° C. and resuspended in TE buffer. The concentration of the RNA was determined by spectrophotometric reading at 260 nm.

7. Isolation of mRNA

Messenger RNA was affinity purified from total RNA using a Pharmacia (Upsalia, Sweden) mRNA purification kit. The total RNA sample in 1 ml of TE buffer was heat denatured at 65° C. for 5 minutes and placed on ice. The salt concentration was adjusted to 0.5M NaCl and the entire sample was applied to the oligo-(dT)-cellulose spun column which had been pre-equilibrated with high salt buffer (0.5M NaCl). The unbound RNA was removed by several washings with high salt buffer followed by low salt buffer (0.1M NaCl). The poly(A)$^+$RNA was recovered by elution with warm no-salt buffer. The washing and elution steps were all performed very quickly by low speed centrifugation of the column. The RNA recovered from the first spun column was subjected to a second round of spun column chromatography to increase the proportion of poly(A)$^+$RNA to over 90% of the sample. The poly(A)$^+$RNA was concentrated by precipitation with glycogen.

8. Construction of cDNA libraries

The cDNA libraries were constructed using mRNA isolated as described above and the Pharmacia (Upsalia, Sweden) You-Prime cDNA Synthesis Kit, according to the manufacturer's instructions. cDNA synthesis was primed with olig-dT. The double stranded cDNA was ligated with Eco RI/Not I adaptors then ligated into the Eco RI site of λ gt11 vector (Promega) at 12° C. for 16 hours. The phage particles were packaged using Packagene® in vitro Packaging System from Promega (Madison, Wis.) according to the manufacturer's instructions. Phage buffer (20 mM Tris-HCl, pH 7.4, 100 mM NaCl, 10 mM MgSO$_4$) to a final volume of 0.5 ml, and 25 µl of chloroform was added to the packaged phage. This was stored at 4° C. for up to 3 weeks.

The packaged phage was titrated by dilution with phage buffer. The phage were used to infect *E. coli* Y1090 host cells, mixed with top agarose (45° C.) containing ampicillin, X-Gal and IPTG and poured onto warm LB plates. The plates were incubated overnight at 37° C. The non-recombinant phages produced blue plaques and recombinants produced clear plaques. The plaques were counted in order to calculate the percentage of recombinants.

The library was plated at a density of 10,000 plaques per 15 cm plate as described above but X-Gal and IPTG were omitted from the top agarose. The plates were incubated at 40° C. until plaques started forming and the plates were overlayed with IPTG impregnated nitrocellulose filters and incubated at 37° C. for 4–5 hours. The antigen positive plaques were identified using the immunological screening procedures described above.

9. Lambda lysates and isolation of lambda DNA

The bacteriophage λ liquid lysates were prepared according to standard procedures as described (Leder et al., *Science* 196:175–177 (1977)).

The procedure used for isolating bacteriophage λ DNA involved chromatography on the resin diethylaminoethyl (DEAE)-cellulose (DE52, Whatman Clifton, N.J., U.S.A.). The DEAE-cellulose reagent (DE52), was prepared according to Benson and Taylor (*Biotechniques*, May–June, 126–127 (1984)), by addition of several volumes of 0.05M HCl to 100 g DE52, until the pH dropped below 4.5. The pH of the solution was then adjusted to 6.8 by the addition of 10M NaOH, and the resin washed several times in L-broth medium. The DE52 solution was stored as a slurry of 60% resin, 40% L-broth, 0.1% sodium azide at 4° C. The resin columns were packed to contain approximately 2 ml of resin as described by Meese et al., (*Nucleic Acids Res.* 18:1923 (1990)). The liquid lysate was applied to the column, allowed to run through and the column washed with L-broth. The runthrough was combined and the phages were precipitated by addition of NaCl to a final concentration of 0.07M and 2 volumes of 100% cold ethanol for 20 minutes at 20° C. Following centrifugation at 12,000×g the resulting pellet was washed in 70% ethanol and resuspended in TE buffer, pH 7.6, containing 0.2% SDS. The phages were lysed by the addition of an equal volume of phenol. The samples were vortexed, centrifuged at 12,000×g and the aqueous layer collected and extracted with phenol again. The phage DNA was precipitated by addition of 2 volumes 100% ethanol and washed twice with 70% and 100% ethanol. The isolated DNA was then digested with restriction enzymes to liberate the inserts which were used for subcloning.

10. Agarose gel electrophoresis and isolation of cDNA inserts

Horizontal agarose gel electrophoresis was the standard method used to separate DNA fragments. Gels of different agarose concentrations were used in different experiments in order to separate DNA molecules in different size ranges (Helling et al., *J. Virol.* 14:1235–1244 (1974)). Typically 0.8–1.2% agarose mini slab gels (mini-sub DNA cell, Bio-Rad Laboratories, Richmond, Calif.) measuring 6.5×10.2× 0.5 cm and containing ethidium bromide at a final concentration of 0.5 µg/ml were run in 1×TBE (89 mM Tris, 89 mM Boric acid, 2.5 mM EDTA, pH 8.2) for 1.5 to 2 hours at a constant voltage of 70–100V.

DNA fragments used for cloning or probing purposes were isolated by elution from low melting agarose gels (BRL Low melting agarose). The bands were visualized under UV illumination and a slice of agarose containing the band of interest was removed using a razor blade. The agarose slice was then placed in a microfuge tube with 150 µl of TE buffer and the agarose melted at 65° C. An equal volume of pre-warmed phenol was then added and the mixture was centrifuged for 3 minutes at 12000×g. The supernatant was then mixed with an equal volume of chloroform and centrifuged for 30 seconds. The DNA was precipitated from the supernatant with 100% ethanol after addition of ¹⁄₁₀ volume 3M sodium acetate and washed in 70% ethanol. The DNA pellet was vacuum dried and resuspended in sterile distilled water. DNA inserts isolated in this way were used for ligations or nick translation.

11. Subcloning of cDNA inserts into plasmid vectors

Either pGEM®-4Z or pBluescript (Stratagene Inc., La Jolla, Calif., U.S.A.) plasmid DNA (20 ng), which had been restricted with an appropriate enzyme, was ligated with 100 ng of the DNA insert of interest that possessed vector compatible ends. The reaction volume was normally 10 µl of a solution containing 50 mM Tris-HCl (pH 7.4), 10 mM MgCl$_2$, 1 mM spermidine, 0.1 mg/ml BSA, 1 mM ATP and 3 units of T4 DNA ligase (Promega, Madison, Wis.). The reaction proceeded at 15° C. for 18 hours if the ligation involved cohesive ends. For blunt end ligations, 6 units of enzyme were used and the reaction was incubated at 4° C. for 24 hours. Controls to test the efficacy of the ligation were required. These controls were vector that had been restricted and religated and vector that had only been restricted.

12. Competent cell preparation, transformation and identification of recombinant plasmids The bacterial strains used for transformation were *E. coli* JM 109 for pGEM®-4Z, JPA 101 for pGEX and XL-Blue for pBluescript. All of these plasmids have ampicillin selection. JM 109 and XL-pBluescript also could be screened for blue/white color. The host strains were maintained on minimal media plates.

For competent cell production, a single colony was selected and grown overnight at 37° C. in L-broth with vigorous shaking. A 1:100 dilution of the overnight culture was grown until the $A_{600}$ reached 0.45–0.55 and the cells were then pelleted by centrifugation at 800×g for 10 minutes at 4° C. The cells were made competent for transformation by resuspension in 50 ml of ice cold, sterile 50 mM $CaCl_2$ and incubation on ice for 1 hour. The cells were again pelleted, then resuspended in 10 ml of prechilled 50 mM $CaCl_2$. The competent cells prepared in this way were stored on ice at 4° C. and used for up to 48 hours after preparation, but their viability began to decline after 24 hours.

For transformation, 300 µl of competent cells were added to 10 µl of ligation mixture, left on ice for 1 hour and then heat shocked at 42° C. for 2 minutes. Following this, 0.3 ml of L-broth was added and the cells were incubated for 1–2 hours at 37° C., after which 0.2 ml was plated onto selective media.

Both pGEM and Bluescript vector systems carry DNA sequences coding for the lacZα-peptide, flanking the multiple cloning site. This arrangement gives rise to a functional α-peptide which is capable of complementing the product of the lacZ M15 gene to produce functional β-galactosidase. Bacterial colonies having the lacZ M15 gene on a F' pilus and also containing pGEM®-4Z or pBluescript plasmid are blue in color when plated on media containing IPTG and 5-dibromo 4-chloro 3-indoyl thiogalactosidase (X-gal). However, when the lacZα-peptide is disrupted by cloning into the multiple cloning region, complementation does not occur and no β-galactosidase activity is produced. Therefore, the colonies containing the recombinant plasmids are white.

JPA 101 cells transformed with recombinant pGEX plasmids were plated on ampicillin containing media and the recombinants confirmed by plasmid isolation, followed by restriction and agarose gel electrophoresis.

13. Production of monoclonal antibodies LpIX-3A and LpIX-4A

Monoclonal antibodes LpIX-3A and LpIX-4A to the rye-grass pollen allergen Lol p IX were produced. A full length cDNA clone 12R (1229 bp) encoding Lol p IX (described in International application PCT AU92/00430, the contents of which are incorporated herein by reference) was digested with the restriction enzyme Hinc II and the 673 base pair fragment 1H was selected after agarase gel electrophoresis. The 1H fragment was subcloned into the pGEX plasmid expression system. The expression of the protein as a fusion with glutathione S-transferase (GST) was carried out according to the procedure outlined by Smith and Johnson (*Gene* 67:31–40 (1988)). Briefly, overnight cultures of *E. coli* with recombinant 12R pGEX-1, 2P pGEX-1 and 1H pGEX-3 plasmids were diluted 1:10 in fresh L-broth and grown for 1 hour at 37° C. with vigorous shaking. Fusion protein production was induced by adding IPTG to 0.1 mM. The cells were grown for a further 4–5 hours after which they were pelleted and resuspended in PBS (150 mM NaCl, 16 mM $Na_2HPO_4$, 4 mM $NaHPO_4$, pH 7.2). The cells were lysed by subjecting the mixture to three freeze-thaw cycles in liquid nitrogen and the supernatant collected after centrifugation.

The supernatant containing the GST-1H fusion protein was applied to the Superdex 75 HR 10/30 column (Pharmacia). The sample was eluted from the column with 50 mM PBS containing 0.02% sodium azide, at a constant flow rate of 1 ml/minute at room temperature. The fractions containing the fusion protein were identified by dotting 5 µl of each fraction onto nitrocellulose membrane (BA 0.45 µm, Schleicher and Schuell) and screening with sara from allergic patients for binding of specific IgE. The protein was concentrated using minicon ultrafree-MC 10000 NM WL filter unit (Millipore, Bedford, Mass, U.S.A.).

Mouse antibodies specific for the GST-1H fusion protein antigens were prepared by immunizing 4 female BALB/c mice with an inter peritoneal (i.p.) injection of 100 µg of FPLC purified GST-1H fusion protein in 0.1 ml PBS and 0.1 ml RIBI adjuvant. Fourteen days later a booster i.p. of the same material was given. After 10 days the mice were bled. The serum was screened for binding to Western blots of total rye-grass pollen proteins and the mice were selected on the basis of this serum binding. Fourteen days later, the mice selected for fusion were given an i.p. booster of 0.2 ml containing 100 µg fusion protein only. Four days later the mouse was sacrificed and the spleen removed for fusion with myeloma cells (a gift from the Veterinary Research Institute, Parkville). The methods used for fusion and culture were based on those of Harlow and Lane (Antibodies, A Laboratory Manual, Cold Spring Harbor Laboratory Press (1988)) using RPMI and Hybridsera (Commonwealth Serum Laboratories, Melbourne, VIC, Australia). Aminopterin selection was used (50×HAT & HT solutions, Flow Laboratories, Scotland, U.K.). The resulting hybridomas were screened for the presence of antibodies by a direct binding ELISA assay. Positive hybridomas were cloned by limiting dilution.

ELISA's were performed using membrane bottomed microtiter plates (Amersham). The antigen, 1 µg of soluble rye-grass pollen proteins, was dotted onto the membrane at the bottom of each well and incubated at room temperature for 15 minutes. After washing wells with PBS, 1% BSA (100 µl) was added and incubated for 30 minutes in order to block non-specific binding sites. The wells were washed 3 times with TPBS and culture supernatants (100 µl) added and incubated at room temperature for 30 minutes. The wells were again washed and incubated with 100 µl HRP-conjugated second antibody (Silenus, Melbourne, VIC, Australia) for 30 minutes. Following 4 washes with TPBS, peroxidase substrate solution containing 4-Chloro-1-naphthol was added and incubated at 37° C. for approximately 5 minutes until the purple color developed.

Monoclonal lines were isotyped using a mouse monoclonal antibody isotyping kit (Amersham International) according to the manufacturer's instructions.

14. Isolation of plasmid DNA

Bacteria containing plasmids of interest were cultured at 37° C. in L-Broth containing the appropriate antibiotic overnight. The cultures were then used for DNA isolations.

(i) Rapid plasmid isolation

This method was developed by Serghini et al. (*Nucleic Acid Res* 17:3604 (1989)) and is for preparing DNA used for routine analysis. One and a half ml culture is transferred to an Eppendorf tube. Cells are pelleted by 3 minute centrifugation at 12,000×g, resuspended in 50 µl TNE (10 mM Tris-HCl pH8, 100 mM NaCl, 1 mM EDTA) and 50 µl mixed (v/v/v) phenol/chloroform/isoamyl alcohol (25/24/1) added. The mixture is vigorously vortexed and centrifuged for 5 minutes at 12,000×g to yield an almost clear supernatant. Fifty µl of aqueous phase is transferred into a fresh centrifuge tube and precipitated with 2M ammonium acetate (final concentration) and 2 volumes of cold 100% ethanol for 15 minutes on ice. The precipitated DNA is collected by 15 minutes centrifugation at 12,000×g, washed with 70% ethanol, dried and dissolved in an appropriate volume of TE (10 mM Tris-HCl pH 8.0, 1 mM EDTA).

(ii) DNA for sequencing

DNA used for sequencing template was isolated and purified according to a protocol provided by Qiagen Inc., (Chatsworth, Calif. U.S.A.). One and a half ml of bacterial culture was pelleted down at 12,000×g for 2 minutes. The pellet was resuspended in 0.3 ml of buffer P1 (100 µg/ml RNase A, 50 mM Tris-HCl pH 8.0, 10 mM EDTA), and 0.3 ml of buffer P2 (200 mM NaOH, 1% SDS) was added to it and mixed. After incubating at room temperature for 5 minutes, 0.3 ml of buffer P3 (2.55M potassium acetate pH4.8) was added, mixed immediately and centrifuged for 15 minutes at 4° C. (12,000×g). The supernatant was removed to a fresh tube and applied to a Qiagen column for purification following the manufacturer's instruction. After eluting from the column, the DNA was precipitated with 0.5 volumes of isopropanol and centrifuged at 12,000×g for 30 minutes. The DNA was then washed with 70% ethanol, air dried for 5 minutes and redissolved in a suitable volume of TE buffer.

15. DNA sequencing

DNA sequencing was carried out using the chain termination method of Sanger et al., (*Proc. Natl. Acad. Sci USA* 74:5463–5467 (1977)). pGEM®-4Z has two priming sites, the Sp6 and T7 promotor primers, which are located at opposite ends of the multiple cloning site. The promotor primers in pBluescript IIKS are T7 and T3.

The double stranded DNA template for sequencing was prepared as described above. The dideoxy sequencing reactions were performed using either T7 polymerase sequencing kit, Deaza T7 polymerase kit of Gene Ataq sequencing kit from Pharmacia (Uppsala, Sweden), according to manufacturer's instructions. The label used was deoxyadenosine 5-α-[$^{35}$S] thiotriphospate, triethylammonium salt (Amersham).

Electrophoresis of sequencing reactions was performed in polyacrylamide gel and IBI Base Runner sequencing apparatus (International Biotechnologies, Inc., Connecticut, Wis., U.S.A.). Gels were cast in 25×60 cm glass plates separated by 0.35 mm plastic spacers. Glass plates were taped together with waterproof tape (Scotch plastic tape No. 471). Typically gels were 6% acrylamide in 7M urea. The gel mixtures were made up using appropriate amounts of Sequagel concentrate and diluent solutions (National Diagnostics, Manville, N.J., U.S.A.), TBE buffer, ammonium persulphate and N,N,N',N',-tetramethylenediamine (TEMED, Bio-Rad). Gels were allowed to polymerize for 90 minutes before beginning prerun. Gels were loaded with loading dye and prerun for 15–30 minutes. The sequencing reactions were then loaded into wells created by the shark's tooth comb and electrophoresis was performed in TBE buffer at 50 W for 2–3 hours. To maximize the amount of sequencing information obtained from each gel a longer run of 5–6 hours was performed. Following electrophoresis, gels were transferred to Whatman paper and were then dried for 2 hours at 80° C. under vacuum on a Bio-Rad gel dryer. Autoradiography was usually performed overnight at room temperature without an intensifying screen. Kodak XAR X-ray film was used.

16. Computer analysis

Sequence analysis was performed using the MELBDB-SYS system—a sequence analysis suite of programs developed in Melbourne Australia at the Walter and Eliza Hall Institute, Ludwig Institute for Cancer Research and the Howard Florey Institute. This incorporates the programs of the following sources: Roger Staden, MRC Labs Cambridge, England; NIH/Los Alamos National Laboratory, U.S.A.; NBRF Protein Identification Resource, Washington, U.S.A.; GENBANK (Los Alamos National Laboratory, U.S.A.); NBRF PIR, PSD-Kyoto (ooi); GBtrans, Swiss-Prot and Doolittle protein databases. During the final searching period EMBL and GENBANK databases were releases 28.0 and 68.0 respectively.

17. Oligonucleotide synthesis

Oligonucleotide primers were constructed based on selected DNA sequences. The primers were synthesized by the phosphoarmidite method, which has been discussed extensively by Winnacker and Dorper (*Anal. Biochem.* 142:78–90 (1982)), using a Pharmacia Geneassembler DNA synthesizer (Pharmacia).

18. Labelling of nucleic acids

Oligonucleotide probes were radiolabelled with $\gamma^{32}$P-ATP (Amersham International) based on the method originally described by Maxam and Gilbert (*Meth. Enzymol* 65:763–774 (1980)). Usually, 20 ng (1 µl) of probe was added to buffer containing 50 mM Tris-HCl (pH 7.5), 10 mM MgCl$_2$ and 1 mM DTT. This was followed by the addition of 40 µCi of label and 5 units of T4 polynucleotide kinase (Pharmacia). The reaction mixture was made up to an appropriate volume with sterile millipore water and incubated for 45 minutes at 37° C. The reaction was stopped by the addition of EDTA to a final concentration of 1 mM.

Free counts were removed by centrifugation of the reaction mixture through a Sephadex G-50 column. The column was prepared by plugging a 1 ml syringe with glass wool and packing the syringe with ml of Sephadex G-50 equilibrated with TE (pH 8.0). The column was then placed in a sterile disposable 10 ml tube and centrifuged at 1,000×g for 1 minute, the mixture was then applied to the column (in a volume <100 µl) and the column recentrifuged at 1,000×g for a further minute. The effluent containing the labelled probe was collected.

Labelling of DNA insert was routinely performed by random priming method (Feinberg and Vogelstein, *Anal. Biochem.* 137:266–267, 1984)). Sixty to 100 ng of dsDNA was denatured by heating at 95° C. for 2 minutes and cooled immediately on ice. The labelling mix (Bresatec) was added containing 12.5 ng random primer, 50 mM Tris-HCl pH 7.5, 10 mM MgCl$_2$, 10 mM DTT, 50 µCi $^{32}$P-dCTP and 5 units of Klenow DNA polymerase I. The reaction was incubated at 40° C. for 20 minutes. The probe was then purified as section described above and heated for 2 minutes at 95° C. to denature the DNA prior to use.

19. Electrophoresis of RNA and Northern blotting

RNA was electrophoresed under denaturing conditions through gels containing formaldehyde (Lehrach et al., *Biochemistry* 16:4743–4745, 1977)). Powdered agarose 1.8 g (Promega) was melted in 110 ml diethylpyrocarbonate (DEPC) treated Millipore water by heating in a microwave oven. After cooling to 60° C., 15 ml of 10×MOPS (0.4M morpholino propanesulfonic acid (MOPS), pH 7.0, 100 mM sodium acetate and 10 mM EDTA, pH 8.0) and 1 drop of DEPC was added. Ten minutes later 4.8 ml of formaldehyde (37% solution in water) was added, mixed and the molten solution poured into an appropriate gel mold. Samples of total RNA from various tissues to be electrophoresed were prepared by mixing 6.2 µl RNA (10–20 µg) with 0.4 µl 1M MOPS, 3.4 µl formaldehyde and 10 µl deionized formamide, followed by incubation at 60° C. for 5 minutes to facilitate denaturation. After chilling the samples on ice, RNA gel loading buffer was added to a final concentration of 1×. Samples were loaded and electrophoresed at 70V for 4 hours.

After electrophoresis, RNA containing gels were soaked for 5 minutes in several changes of autoclaved Millipore water. The RNA was transferred to a nylon membrane, Hybond-N+ (Amersham, Arlington Heights, Ill.) under vacuum using VacuGene blotting system (Pharmacia, Upsalla, Sweden). After 3–4 hours transferring, the filter was dried at room temperature and exposed to UV light for 5 minutes in order to crosslink the RNA to the membrane.

20. Hybridization

A DNA-target DNA probe protocol was generally used for hybridization of DNA blots or filters with a dsDNA probe. The prehybridization was carried out in hybridization buffer containing 2× SSPE (0.18M NaCl, 10 mM NAPO$_4$, 1 mM EDTA), 7% SDS, 0.5% non fat milk powder, 1% polyethylene glycol 20000 and 0.5 mg/ml non-homologous carrier DNA (Sigma) at 68° C. for 4 hours. Following prehybridization, the hybridization was performed in fresh hybridization buffer containing the $^{32}$P-labelled dsDNA probe at 68° C. for 16 hours.

After hybridization, the blot or filter was rinsed briefly in 2× SSC (0.15M NaCl, 15 mM Na$_3$-citrate), then washed in 2× SSC, 0.1% SDS with vigorous agitation at room temperature for 15 to 30 minutes. A final wash was performed in pre-heated 1× SSC, 0.1% SDS at 68° C. for 15 minutes. The blot was then wrapped in polyethylene film, and autoradiography was performed at –70° C. using X-ray film and intensifying screen.

For hybridization of RNA blots, the prehybridization and hybridization was carried out in 2× SSPE, 7% SDS, 0.5% non fat milk powder, 1% polyethylene glycol 20000, 50% deionized formamide and 0.5 mg/ml non-homologous carrier DNA at 43° C. for 4 hours and 16 hours respectively. The washing and autoradiography of the hybridized blot was performed as described above.

A different protocol was used for hybridization with oligonucleotide probes. The prehybridization and hybridization was performed in 5× SSPE, 7% SDS, 0.5% skim milk powder, 1% polyethylene glycol 20000 and 0.5 mg/ml non-homologous carrier DNA (Sigma, St. Louis, Mo.) at appropriate T$_m$ (Bolton and McCarthy (1962) PNAS 48:1390). The hybridized membrane was rinsed briefly in 3× SSC and washed in 3× SSC, 0.1% SDS at room temperature with vigorous shaking for 15 minutes. This was followed by another was in pre-heated 2× SSC, 0.1% SDS at hybridization temperature for 15 minutes. After rinsing briefly in 1× SSC, 0.1% SDS, the membrane was then exposed to the X-ray film at –70° C.

C. RESULTS

1. Characterization of Sor h I and its tissue specificity by immunoblotting

The major allergen of *S. halepense*, Sor h I, like its Group I counterparts, has a molecular weight around 35 kD when analysed by SDS-PAGE. It shows reactivity with Group I antibodies raised against Lol p I and Cyn d I, and IgE from the sera of grass pollen allergic individuals. Immunoblotting with these monoclonal antibodies showed reactivity only with pollen proteins and not with proteins from other plant tissues including leaves, roots or shoots. These studies also revealed that the predominant IgE binding components among pollen proteins was Sor h I but there was also binding to components in other tissues (FIG. 1).

Figure 1F:
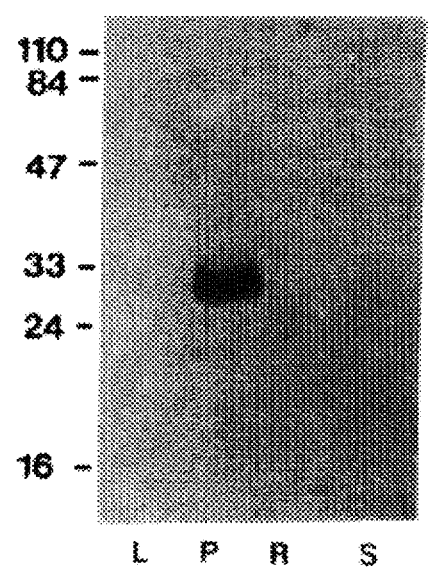
Figure 2A:
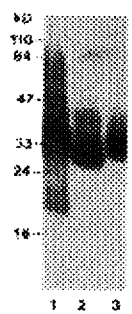
FIG. 2 shows immunoblot analysis of Johnson grass pollen proteins from different suppliers. The blots were probed with monoclonal antibodies as follows. Panel A:FMC-A1; Panel B:CdI-1D1; Panel C:CdI-3A2; Panel D:CdI-4D2; Panel E:FMC-A7; Panel F:LpIX-3A; and Panel G:LpIX-4A.
Figure 2B:
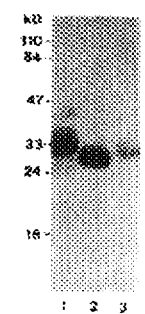
Figure 2C:
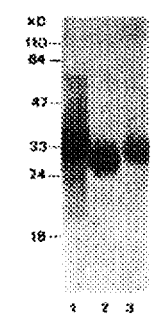
Figure 2D:
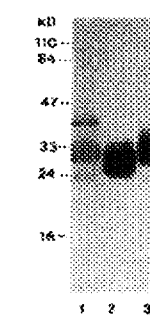
Figure 2E:
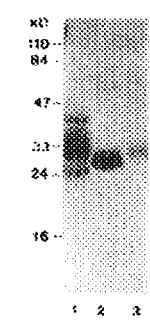
Figure 2F:
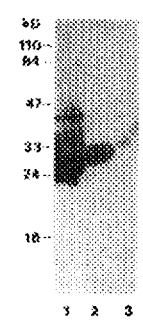
Figure 2G:
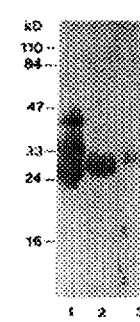

As shown in FIG. 1, proteins isolated from Johnson grass, leaves (L), pollen (P), roots (R), and seeds (S) were separated by SDS-PAGE. Panel A is protein profiles revealed by Coomassie Brilliant Blue R250 staining. Panels B-F show Western blots immunoprobed with monoclonal antibodies or IgE and detected using peroxidase-labelled secondary antibody. Panel B is antibodies from pooled sera of grass pollen allergic individuals. Panel C, mAb FMC-A1; Panel D, mAb CdI-1D1; Panel E, mAb CdI-3A2; and Panel F, mAb CdI-4D2.

2. Variations in antibody binding to Johnson grass pollen extracts

One observation of antibody specificity in Johnson grass concerned variations in the antigenic profile of proteins from pollen samples from different suppliers. In order to test for protein variability, soluble Johnson grass pollen proteins were isolated from pollen obtained from three different suppliers. Coomassie brilliant blue staining following SDS-PAGE separation of proteins, revealed that all 3 samples had different protein profiles (FIG. 2). Immunoprobing of Western blots of these proteins with mAbs against different allergens, revealed differences in the binding patterns of antibodies. (Panel A: FMC-A; Panel B: CdI-1D1; Panel C: CdI-3A2; Panel D: CdI-4D2; Panel E: FMC-A7; Panel F: LpIX-3A; and Panel G: LpIX-4A). When the total proteins of this pollen from supplier 1 were separated by SDS-PAGE, blotted and screened with mAbs Lp IX-3A and Lp IX-4A, binding to three components with MW of 28, 33 and 40 kD was observed. The binding of mAbs Lp IX-3A and Lp IX-4A to the samples from suppliers 2 and 3 was to a single band around 30 kD. mAbs Lp IX-3A and LP IX-4A, bound weakly to the sample from supplier 3 (FIG. 2).

3. Isolation and characterization of Johnson grass cDNA clones

A *S. halepense* cDNA expression library in λ gt11 was screened with anti-Group I antibodies raised against ryegrass and Bermuda grass. Three positive clones, 1S, 2S and 3S were plaque-purified and tested for IgE binding with grass pollen allergic sera, which showed reactivity to soluble Johnson grass pollen proteins on Western blots. Only one clone, 3S, showed reactivity with IgE antibodies. None of the clones showed reactivity with mAbs Lp IX-3A and Lp IX-4A. The antibody binding data for the three clones is summarized in Table I.

Restriction enzyme analysis of the 3 clones revealed that clone 3S contained the largest insert of approximately 1100 nucleotides with 1S and 2S containing inserts of approximately 800 and approximately 400 nucleotides respectively.

TABLE I

| Antibody binding to Johnson grass cDNA clones | | | |
|---|---|---|---|
| antibody | clone 1S | clone 2S | clone 3S |
| serum IgE | – | – | + |
| FMC-A1 | + | – | + |
| FMC-A7 | + | + | + |
| LpIX-3A | – | – | – |
| LpIX-4A | – | – | – |
| CdI-1D1 | – | + | – |
| CdI-3A2 | – | + | + |
| CdI-4D2 | – | + | – |

4. Identity of the cloned allergen 3S

Figure 3:
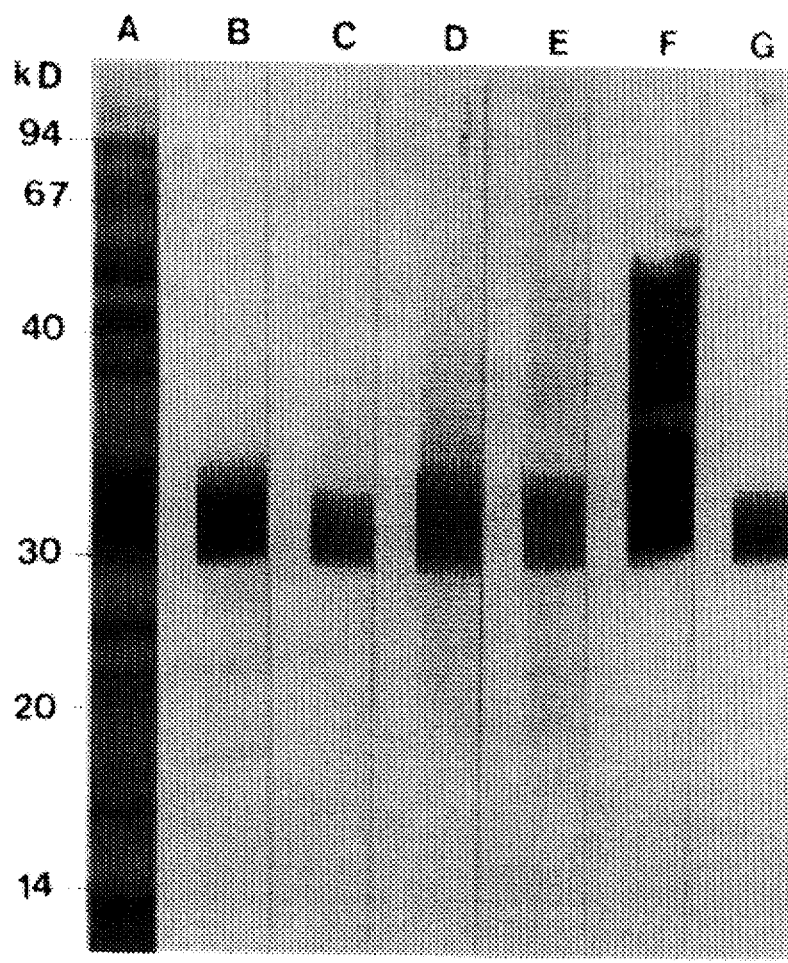
FIG. 3 shows Western blots of soluble Johnson grass pollen proteins probed with monoclonal antibodies and sera from allergic patients.

Since the recombinant clone 3S was isolated by using anti-Group I mAbs, the specificity of these mAbs on Western blots of Johnson grass pollen proteins indicates the clone's relationship to the native allergen. Immunoprobing of Western blots of Johnson grass pollen proteins with anti-rye-grass mAb FMC-A1, revealed binding to components in the 28 to 35 kDa region. Molecular weight is denoted on the left (kD) in FIG. 3. In Lane A, the proteins were separated by SDS-PAGE and visualized by Coomassie Brilliant Blue R250 staining. Lanes B–G show Western blots immunoprobed with mAbs or IgE and detected using peroxidase-labelled secondary antibody except where indicated. Lane B: mAb FMC-A1; Lane C: mAb CdI-1D1; Lane D: mAb CdI-3A2; and Lane E: mAb CdI-4D2. In Lane F, IgE antibodies from pooled sera of grass pollen allergic individuals was used. Lane G shows IgE antibodies affinity purified using fusion protein of clone 3S as immunosorbent. The binding of IgE is detected with $^{125}$I-labelled anti-human IgE. The same binding pattern was observed for anti-Bermuda grass Group I antibodies CdI-1D1, CdI-3A2 and CdI-4D2 (FIG. 3).

In order to identify the protein band, corresponding to the protein encoded by clone 3S on the Western blot of Johnson grass proteins, IgE antibodies affinity purified by using 3S fusion protein as immunosorbent, were used for screening. This revealed binding to a band of the Sor h I range of approximately 35 kD (FIG. 3).

5. Sequence analysis of Sor h I cDNA

Figure 4:
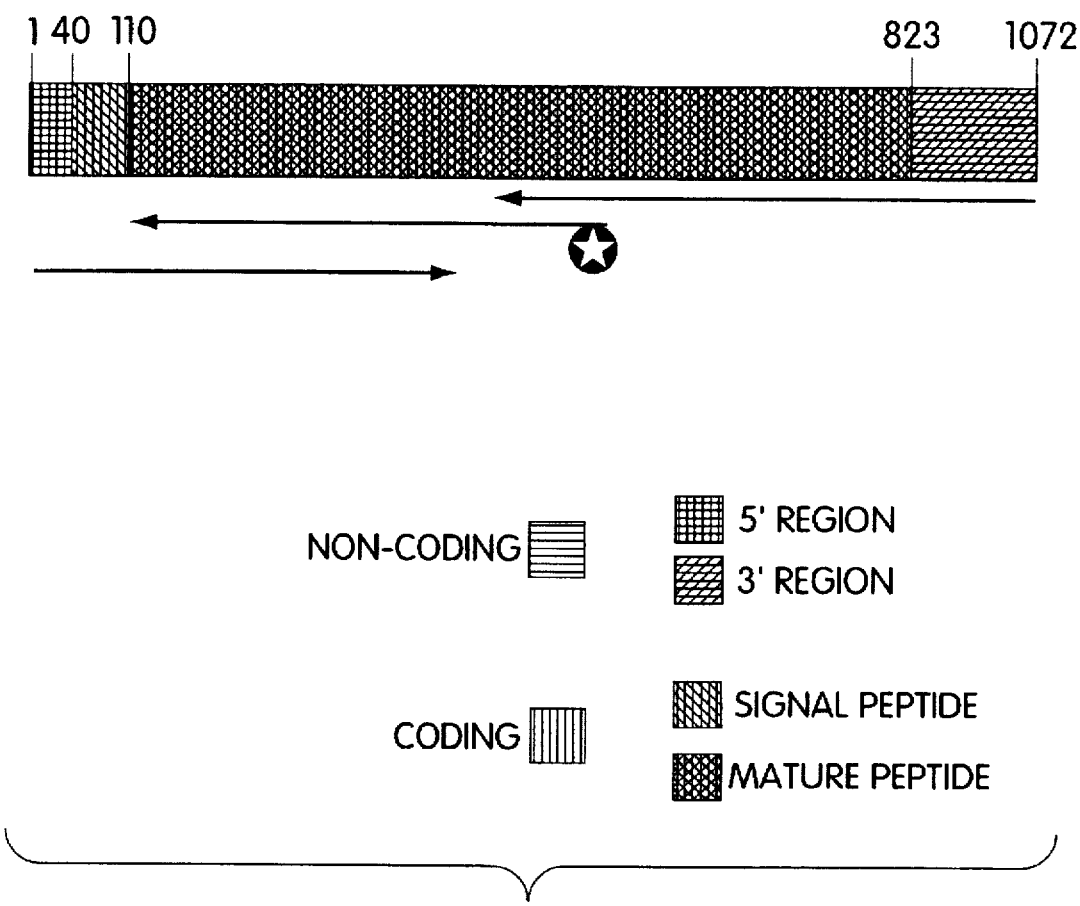
FIG. 4 is a schematic representation of the sequencing strategy and map of Sor h I clone 3S.

All three cDNA clones 1S-3S were completely sequenced. A custom primer of 16 nucleotides, which has the sequence 5'-TCGCCACCCTTCTCCT-3' (SEQ ID NO: 14) and corresponds to non-coding strand sequence homologous to nucleotides 538-653 of clone 3S shown in FIG. 5, was used to sequence clone 3S. The initial sequencing strategy for clone 3S is shown in FIG. 4. The location of the above mentioned synthetic primer is denoted by an asterisk. Both strands of clone 3S were subsequently resequenced completely using synthetic primers 1004-1009, 1014 and 1015. All primers were based on the Sor h I sequence as shown in FIG. 5. Primer 1004, 5'-CCTGTTGGCTTACCGTACCA-3' (SEQ ID NO: 15), corresponds to non-coding strand sequence homologous to nucleotides 181-200 of FIG. 5. Primer 1005, 5'-CAACCTCCCCATCTTCAA-3' (SEQ ID NO: 16), corresponds to nucleotides 282-299 of FIG. 5. Primer 1006, 5'-GGCGATTTGCTCGTAGTTCAT-3' (SEQ ID NO: 17), corresponds to the non-coding strand sequence homologous to nucleotides 391-411 of FIG. 5. Primer 1007, 5'-GGCATCATCGACATGAAGTTC-3' (SEQ ID NO: 18), corresponds to nucleotides 490-510 of FIG. 5. Primer 1008, 5'-TACGCGTCGCCACCCTTCTCCTT-3', corresponds to the non-coding strand sequence homologous to nucleotides 637-659 of FIG. 5. Primer 1009, 5'-GCCAATCAAGTTTCCCGTCA-3' (SEQ ID NO: 19), corresponds to nucleotides 711-730 of FIG. 5. Primer 1014, 5'GAACTTCATGTCGATGATGCC-3' (SEQ ID NO: 20), corresponds to the non-coding strand sequence homologous to nucleotides 490-510 of FIG. 5. Primer 1015, 5'-CTTGTCGCTGTCCTTCCTCC-3' (SEQ ID NO: 21), corresponds to the non-coding strand sequence homologous to nucleotides 692-711 of FIG. 5.

Sequencing was carried out using the T3 and T7 primers, as well a the custom primer. Sequencing strategy is represented by the arrows. The coding region between nucleotides 40-108 corresponds to the signal peptide and that between 109 and 822 encodes the mature protein.

The DNA and the deduced amino acid sequence of the major allergen of Johnson grass encoded by clone 3S is shown in FIG. 5. Sequence analysis of clone 3S revealed that the insert is 1072 nucleotides long. The sequence contains 3 possible in-frame ATG start codons at positions 25, 37 and 40. None of the potential translation initiation sites conformed to the consensus plant sequence of AACA<u>ATG</u>GC (Latake et al. (1987) *EMBO J.* 6:43–48). Therefore, by comparison with Lol p I, the ATG codon at position 40 is proposed as the site for translation initiation. This corresponds to an open reading frame of 783 nucleotides terminating with a TAA stop codon at position 823 (designated by an asterisk in FIG. 5) and coding for a protein of 261 amino acids. This open reading frame is GC rich (62% GC).

Figure 6:
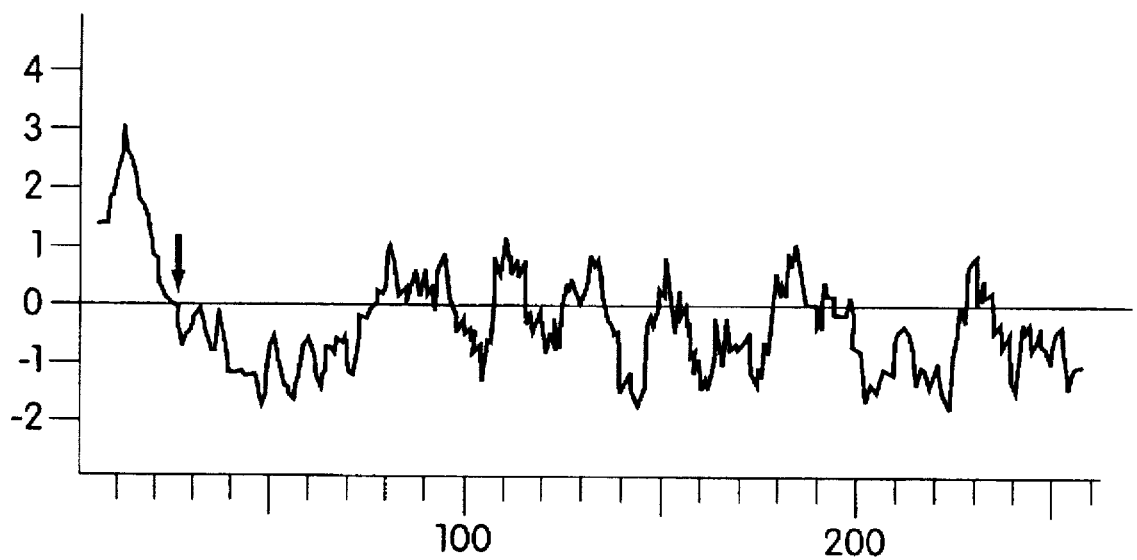
FIG. 6 is the hydrophobicity profile of Sor h I.

The predicted amino acid sequence has a putative signal peptide sequence of 23 amino acids (designated by negative numbers in FIG. 5). Alternatively, the leader sequence could be composed of 28 or 24 amino acids, if the codons beginning at nucleotides 25 or 37, respectively, encode the initiating methionine. The hydrophobicity profile of the predicted amino acid sequence of Sor h I (FIG. 6) is based on the method of Kyte and Doolittle (*J. Mol. Biol.*, 157:105–132 (1982)), with a window of 7 amino acids. Although there is no N-terminal amino acid sequence data available for Sor h I, the point of predicted cleavage of the hydrophobic signal peptide is indicated by the arrow. This signal peptide contains small chain amino acids in positions −1 and −3 relative to the peptide cleavage site, as has been noted for other signal peptides (Von Heijne (1984) *J. Mol. Biol.* 173:243–251). This is indicative of a mature processed protein of 238 amino acids which would have a calculated molecular mass of 25.8 kD. The recombinant protein has a predicted pI value of 7.5, which is higher than that of Lol p I.

There is one possible asparagine-linked glycosylation site at the asparagine residue in position 9 (noted in bold type in FIG. 5) in the hydrophilic region of the protein, which conforms to the consensus sequence Asn-X-Ser/Thr. The sequence of clone 2S corresponds to 451 nucleotides between positions 594 and 945 in the 3S sequence. The nucleotide sequence of clone 1S does not share any homology with clones 2S and 3S and appears to encode an antigen that is distinct from Sor h I.

6. Comparison of Sor h I with Lol p I

The comparison of the nucleotide and the deduced amino acid sequences of Sor h I and Lol p I revealed significant homology. The coding region at nucleotide level shows 78% identity between the two sequences (FIG. 7, SEQ ID NO: 1 and SEQ ID NO: 3). The 214 nucleotide difference in the coding region results in 77 amino acid differences, 18 of which are conservative substitutions. In FIG. 7, the nucleotide sequences are broken into codons, have gaps inserted, and are aligned within the translated region to show maximum similarity. The Lol p I sequence is that of Griffith et al. (*FEBS Lett.* 279:210–215 (1991)). Numerical values at the end of each line refer to the number of nucleotide residues from the first nucleotide of each clone.

The recombinant proteins encoded by rye-grass and Johnson grass clones are similar to their amino acid compositions (Table II). They are both rich in glycine (Sor h I 12.6%; Lol p I 11.4%) and lysine (Sor h I 10.7%; Lol p I 10.3%). Lol p I, with a total of 263 amino acids in the primary structure, contains two more residues than Sor h I. These correspond to calculated molecular weights of 28.3 kD for recombinant Lol p I and 28.1 kD for Sor h I. The calculated pI values are 6.8 for Lol p I and 7.5 for Sor h I.

TABLE II

The amino acid composition of recombinant Lol p I* and Sor h I.

| Amino Acid | Lol p I 263 Amino acids MW:28343 Dalton | | | | Sor h I 261 Amino acids MW:28129 Dalton | | | |
|---|---|---|---|---|---|---|---|---|
| | n | n (%) | MW | MW (%) | n | n (%) | MW | MW (%) |
| A | 21 | 8.0 | 1491 | 5.3 | 26 | 10.0 | 1846 | 6.6 |
| C | 7 | 2.7 | 721 | 2.5 | 8 | 3.1 | 824 | 2.9 |

TABLE II-continued

The amino acid composition of recombinant Lol p I* and Sor h I.

| Amino Acid | Lol p I 263 Amino acids MW:28343 Dalton | | | | Sor h I 261 Amino acids MW:28129 Dalton | | | |
|---|---|---|---|---|---|---|---|---|
| | n | n (%) | MW | MW (%) | n | n (%) | MW | MW (%) |
| D | 19 | 7.2 | 2185 | 7.7 | 18 | 6.9 | 2070 | 7.4 |
| E | 18 | 6.8 | 2322 | 8.2 | 14 | 5.4 | 1806 | 6.4 |
| F | 10 | 3.8 | 1470 | 5.2 | 9 | 3.4 | 1323 | 4.7 |
| G | 30 | 11.4 | 1710 | 6.0 | 32 | 12.3 | 1824 | 6.5 |
| H | 4 | 1.5 | 548 | 1.9 | 4 | 1.5 | 548 | 2.0 |
| I | 11 | 4.2 | 1243 | 4.4 | 12 | 4.6 | 1357 | 4.8 |
| K | 27 | 10.3 | 3458 | 12.2 | 28 | 10.7 | 3586 | 12.8 |
| L | 13 | 4.9 | 1470 | 5.2 | 12 | 4.5 | 1357 | 4.8 |
| M | 3 | 1.1 | 393 | 1.4 | 6 | 2.3 | 786 | 2.8 |
| N | 7 | 2.7 | 798 | 2.8 | 8 | 3.1 | 912 | 3.2 |
| P | 16 | 6.1 | 1552 | 5.5 | 13 | 5.0 | 1261 | 4.5 |
| Q | 2 | 0.8 | 256 | 0.9 | 4 | 1.5 | 512 | 1.8 |
| R | 6 | 2.3 | 936 | 3.3 | 5 | 1.9 | 780 | 2.8 |
| S | 17 | 6.5 | 1479 | 5.2 | 9 | 3.4 | 783 | 2.8 |
| T | 18 | 6.8 | 1818 | 6.4 | 15 | 5.8 | 1515 | 5.4 |
| V | 19 | 7.2 | 1882 | 6.6 | 20 | 7.7 | 1981 | 7.0 |
| W | 6 | 2.3 | 1116 | 3.9 | 7 | 2.7 | 1302 | 4.6 |
| Y | 9 | 3.4 | 1467 | 5.2 | 11 | 4.2 | 1793 | 6.4 |

*The amino acid composition of Lol p I is that of rye-grass cDNA clone according to Griffith et al., supra, (1991) and is presented for comparison.

Comparison of the two deduced amino acid sequences show 77% homology and 70% identity (FIG. 8, SEQ ID NO: 2 and SEQ ID NO: 4). Identical residues are shown by colons. The similar residues between the two sequences are indicated by the lowercase letter "s". The following residues were considered to be similar: A,S,T; D,E; N,Q; R,K; I,L,M,V; F,Y,W. The asterisk represents a blank that has been inserted to maximize homology. The amino acid sequence of Lol p I (SEQ ID NO: 4) is that of rye-grass clone according to Griffith et al., supra, (1991). When the N-terminal regions of these sequences (Lol p I, SEQ ID NO: 5; and Sor h I, SEQ ID NO: 7) are compared with the N-terminal sequence (obtained by protein sequencing) of the Group I allergen of Bermuda grass Cyn d I (SEQ ID NO: 6), it can be seen that the three sequences show homology in this region (Table III). The identity in this region between Lol p I and Cyn d I is 70%; Lol p I and Sor h I 63%; and Cyn d I and Sor h I 59%. The entire primary sequence of Cyn d I is also likely to show overall homology with the other two Group I allergens. This is suggested by the cross-reactivity of the mAbs and the similarity of the amino acid composition reported by Matthiesen et al., (J. Allergy Clin Immunol. 88:763–774 (1991)) to Lol p I and Sor h I.

TABLE III

The N-terminal sequences of known Group I allergens.

| Allergen | N-terminal sequence |
|---|---|
| Lol p I* | I A K V P P G P N I T A E Y G D K W L D A K S T W Y G |
| Cyn d I** | A M G D K P G P X I T A T Y G D K W L D A K A T F Y G |
| Sor h I | P P K V A P G K N I T A T Y G S D W L E R K A T W Y G |

Differing residues in each sequence are designated by bold type.
Lol p I* sequence is according to Cottam et al., Biochem J. 234:305–310 (1986); Perez et al., J. Biol. Chem. 265:16210–16215 (1990); and Griffith et al., supra, (1991).
Cyn d I** sequence is according to Matthiesen et al., supra, (1991). The X in the sequence represents a proposed glycosylation site (presumably N).

7. Sequence comparison of the region containing the allergenically important site The sequences of the regions identified as allergenic determinants of five Group I allergens (i.e., Lol p I, SEQ ID NO: 8; Fes e I, SEQ ID NO: 9; Agr a I, SEQ ID NO: 10; Poa p I, SEQ ID NO: 11; Ant o I, SEQ ID NO: 12), all members of the subfamily Pooideae, were identified by generating and sequencing cleavage fragments (Esch and Klapper, Molecular Immunol. 26:557–561, (1989)). A comparison of these with the corresponding region in Sor h I (SEQ ID NO: 13) which was deduced from the nucleotide sequence, is shown in Table IV. Comparison with these sequences showed a high degree of homology among the peptides in this region. The Sor h I sequence showed identity with Lol p I in 22 out of the 28 amino acids in this region with six differences being detected at positions 1, 9, 10, 11, 24 and 15. Three of these changes at position 9, 24 and 26 were conservative whereby Ser was substituted by Thr, in comparison to Lol p I.

TABLE IV

Comparison of amino acid sequences of allergenically active Group I peptides with that of Sor h I.

| SPECIES | ALLERGEN | AMINO ACID SEQUENCE |
|---|---|---|
| Lolium perenne | Lol p I | Y T T E G G T K S E V E D V I P E G W K A D T S Y S A K |
| Festuca elatior | Fes e I | Y T T E G G T K S E A E D V I P E G W K |
| Agrostis alba | Agr a I | Y T T E G G T K A E A E D V I P E G W K A D T S Y E |
| Poa pratensis | Poa p I | Y T T E G G T K A E A E D V I P E G W K V D T S Y E |
| Anthoxanthum odoratum | Ant o I | I T T E G G K K V E A E D V I P E G W K A D T S Y E |
| Sorghum halepense* | Sor h I | I T T E G G T K T A Y E D V I P E G W K A D T T Y T A K |

Bold letters denote those amino acid residues which differ from Lol p I.
*All the sequences, with the exception of Sorghum halepenseg, were obtained by protein sequencing (Esch and Klapper, supra, 1989) and are presented here for comparison.

Although there was extensive homology between the allergenic determinants, studies comparing IgE reactivity of Lol p I and Sor h I clones did not reveal concordant binding. Out of the 30 grass allergic sera tested for reactivity with Lol p I cDNA 13R and Sor h I cDNA 3S, 28 showed reactivity with the protein produced by Lol p I cDNA, whereas only 2 showed reactivity with that of Sor h I cDNA. The 2 Sor h I reactive sera also showed reactivity with Lol p I.

Although the invention has been described with reference to its preferred embodiments, other embodiments can achieve the same results. Those skilled in the art will recognize or be able to ascertain by using no more than routine experimentation, numerous equivalents to the specific embodiments described herein. Such equivalents are considered to be within the scope of this invention and are encompassed by the following claims.

What is claimed:

1. An isolated nucleic acid comprising a nucleotide sequence coding for a Johnson grass pollen allergen Sor h I, wherein said nucleotide sequence is selected from the group consisting of the nucleotide sequence shown in FIG. 5 (SEQ ID NO: 1) and the coding region of the nucleotide sequence shown in FIG. 5 (SEQ ID NO: 1).

2. An isolated nucleic acid comprising a nucleotide sequence coding for a mature Johnson grass pollen allergen Sor h I, wherein the mature allergen comprises amino acid residues 1–238 of the amino acid sequence shown in FIG. 5 (SEQ ID NO: 2).

3. An isolated nucleic acid of claim 2 comprising nucleotide bases 109–822 of the nucleotide sequence shown in FIG. 5 (SEQ ID NO: 1).

4. An isolated nucleic acid of claim 1 wherein said nucleotide sequence comprises nucleotide bases selected from the group consisting of: bases 25–822 of the nucleotide sequence of FIG. 5 (SEQ ID NO: 1); bases 37–822 of the nucleotide sequence of FIG. 5 (SEQ ID NO: 1); and bases 40–822 of the nucleotide sequence of FIG. 5 (SEQ ID NO: 1).

5. An expression vector comprising a nucleic acid of claim 1.

6. An expression vector comprising nucleic acid of claim 2.

7. A host cell transformed to express a protein encoded by the nucleic acid of any one of claims 1–3 and 4.

8. A method of producing a Johnson grass pollen allergen, Sor h I, comprising the steps of:

a) culturing a host cell transformed with DNA comprising the nucleotide sequence shown in FIG. 5 (SEQ ID NO: 1), or the coding region thereof, in an appropriate medium to produce a mixture of cells and medium containing Sor h I protein; and b) purifying said mixture to produce substantially pure Sor h I protein.

9. A host cell transformed with a vector containing the cDNA insert of Sor h I clone 3S, said host cell having ATCC Deposit No. 69106 deposited Oct. 28, 1992.

10. An isolated nucleic acid comprising a nucleotide sequence coding for a Johnson grass pollen allergen Sor h I having the amino acid sequence shown in FIG. 5 (SEQ ID NO: 2).

11. An isolated nucleic acid comprising a nucleotide sequence coding for a naturally occurring polymorphic variant of a Johnson grass pollen allergen Sor h I, wherein the nucleotide sequence differs due to natural allelic variation from the nucleotide sequence shown in FIG. 5 (SEQ ID NO: 1).

12. An isolated nucleic acid comprising a nucleotide sequence coding for a protein allergen, said nucleotide sequence having sufficient homology to hybridize in 1×SSC, 0.1% SDS at 68° C. for at least 15 minutes to the nucleotide sequence shown in FIG. 5 (SEQ ID NO: 1), with the proviso that the nucleic acid is not from *Lolium perenne* or *Cynodon dactylon*.

13. An isolated nucleic acid encoding a protein allergen comprising at least one T cell epitope present in a Johnson grass pollen allergen, Sor h I, wherein said Sor h I allergen comprises the amino acid sequence shown in FIG. 5 (SEQ ID NO: 2), with the proviso that the nucleic acid is not from *Lolium perenne* or *Cynodon dactylon*.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 1072 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 37..822

( i x ) FEATURE:
( A ) NAME/KEY: mat_peptide
( B ) LOCATION: 109..822

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GCGGCCGCAA | ACGATCGAAG | GAAGATGGGA | GTGAACATG | ATG | TCG | TGG | TCG | ATG | | | | | | | | 54 |
| | | | | Met | Ser | Trp | Ser | Met | | | | | | | | |
| | | | | -23 | | | | -20 | | | | | | | | |
| CAG | GTG | GCG | TTG | GTG | GTG | GCG | CTG | GCG | TTT | CTG | GTG | GGC | GGC | GCA | TGG | 102 |
| Gln | Val | Ala | Leu | Val | Val | Ala | Leu | Ala | Phe | Leu | Val | Gly | Gly | Ala | Trp | |
| | | | -15 | | | | | -10 | | | | | | -5 | | |
| TGC | GGT | CCT | CCC | AAG | GTT | GCC | CCG | GGC | AAG | AAC | ATC | ACG | GCC | ACC | TAC | 150 |
| Cys | Gly | Pro | Pro | Lys | Val | Ala | Pro | Gly | Lys | Asn | Ile | Thr | Ala | Thr | Tyr | |
| | | 1 | | | 5 | | | | | 10 | | | | | | |
| GGC | AGC | GAC | TGG | CTG | GAA | CGG | AAG | GCA | ACA | TGG | TAC | GGT | AAG | CCA | ACA | 198 |
| Gly | Ser | Asp | Trp | Leu | Glu | Arg | Lys | Ala | Thr | Trp | Tyr | Gly | Lys | Pro | Thr | |
| 15 | | | | | 20 | | | | | 25 | | | | | 30 | |
| GGT | GCC | GGC | CCC | GAC | GAC | AAC | GGC | GGC | GCA | TGT | GGT | TAC | AAG | GAT | GTG | 246 |
| Gly | Ala | Gly | Pro | Asp | Asp | Asn | Gly | Gly | Ala | Cys | Gly | Tyr | Lys | Asp | Val | |
| | | | | 35 | | | | | 40 | | | | | 45 | | |
| AAC | AAG | GCC | CCC | TTC | AAC | AGC | ATG | GGC | GCG | TGC | GGC | AAC | CTC | CCC | ATC | 294 |
| Asn | Lys | Ala | Pro | Phe | Asn | Ser | Met | Gly | Ala | Cys | Gly | Asn | Leu | Pro | Ile | |
| | | | | 50 | | | | | 55 | | | | | 60 | | |
| TTC | AAG | GAC | GGC | CTC | GGC | TGC | GGC | TCC | TGC | TTT | GAG | ATC | AAG | TGT | GAC | 342 |
| Phe | Lys | Asp | Gly | Leu | Gly | Cys | Gly | Ser | Cys | Phe | Glu | Ile | Lys | Cys | Asp | |
| | | | 65 | | | | | 70 | | | | | 75 | | | |
| AAG | CCG | GCC | GAG | TGC | TCC | GGC | GAG | GCC | GTG | GTG | GTG | CAC | ATC | ACG | GAC | 390 |
| Lys | Pro | Ala | Glu | Cys | Ser | Gly | Glu | Ala | Val | Val | Val | His | Ile | Thr | Asp | |
| | 80 | | | | | 85 | | | | | 90 | | | | | |
| ATG | AAC | TAC | GAG | CAA | ATC | GCC | GCC | TAC | CAC | TTC | GAC | CTG | GCC | GGC | ACG | 438 |
| Met | Asn | Tyr | Glu | Gln | Ile | Ala | Ala | Tyr | His | Phe | Asp | Leu | Ala | Gly | Thr | |
| 95 | | | | | 100 | | | | | 105 | | | | | 110 | |
| GCG | TTC | GGC | GCC | ATG | GCC | AAG | AAG | GGC | GAG | GAG | GAG | AAG | CTG | CGC | AAG | 486 |
| Ala | Phe | Gly | Ala | Met | Ala | Lys | Lys | Gly | Glu | Glu | Glu | Lys | Leu | Arg | Lys | |
| | | | | 115 | | | | | 120 | | | | | 125 | | |
| GCG | GGC | ATC | ATC | GAC | ATG | AAG | TTC | CGC | CGG | GTC | AAG | TGC | AAG | TAC | GGC | 534 |
| Ala | Gly | Ile | Ile | Asp | Met | Lys | Phe | Arg | Arg | Val | Lys | Cys | Lys | Tyr | Gly | |
| | | | 130 | | | | | 135 | | | | | 140 | | | |
| GAA | AAG | GTC | ACC | TTC | CAC | GTG | GAG | AAG | GGG | AGC | AAC | CCC | AAC | TAC | CTG | 582 |
| Glu | Lys | Val | Thr | Phe | His | Val | Glu | Lys | Gly | Ser | Asn | Pro | Asn | Tyr | Leu | |
| | | 145 | | | | | 150 | | | | | 155 | | | | |
| GCT | CTG | TTG | GTC | AAG | TAC | GTC | GAC | GGC | GAC | GGT | GAC | GTT | GTG | GGG | GTG | 630 |
| Ala | Leu | Leu | Val | Lys | Tyr | Val | Asp | Gly | Asp | Gly | Asp | Val | Val | Gly | Val | |
| | | 160 | | | | | 165 | | | | | 170 | | | | |

```
GAC ATC AAG GAG AAG GGT GGC GAC GCG TAC CAG CCC CTC AAG CAC TCC    678
Asp Ile Lys Glu Lys Gly Gly Asp Ala Tyr Gln Pro Leu Lys His Ser
175             180                 185                 190

TGG GGC GCT ATC TGG AGG AAG GAC AGC GAC AAG CCA ATC AAG TTT CCC    726
Trp Gly Ala Ile Trp Arg Lys Asp Ser Asp Lys Pro Ile Lys Phe Pro
                195                 200                 205

GTC ACC GTC CAA ATC ACC ACC GAG GGA GGC ACC AAG ACC GCC TAC GAA    774
Val Thr Val Gln Ile Thr Thr Glu Gly Gly Thr Lys Thr Ala Tyr Glu
            210                 215                 220

GAC GTC ATC CCC GAA GGC TGG AAG GCC GAC ACC ACC TAC ACC GCC AAA    822
Asp Val Ile Pro Glu Gly Trp Lys Ala Asp Thr Thr Tyr Thr Ala Lys
        225                 230                 235

TAAACTGTCC AACAGACCTA ACGCTGCTCT GGGCTCGGTT GGATTGGATC CCAACTTCCC    882

AAGCAATGCA TTACACTTAC GCATGCATCG ATCCATGCAC AATATCTATT TTTTACTGC     942

TGCTACTGCT ACGACAATGT CCTCCTTTGT CCTCTCCATA TATAGCTAGA GTCAGGCTCC   1002

GCTCTCTTAT ATTATTATTA TATAAGATAA GAAATAGGAG AGAGAGGAGA GAGACCGAGT   1062

AAGCGGGCGG                                                           1072
```

( 2 ) INFORMATION FOR SEQ ID NO:2:

( i ) SEQUENCE CHARACTERISTICS:
( A ) LENGTH: 261 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ser Trp Ser Met Gln Val Ala Leu Val Val Ala Leu Ala Phe Leu
-23         -20                 -15                 -10

Val Gly Gly Ala Trp Cys Gly Pro Pro Lys Val Ala Pro Gly Lys Asn
        -5                  1                   5

Ile Thr Ala Thr Tyr Gly Ser Asp Trp Leu Glu Arg Lys Ala Thr Trp
10                  15                  20                  25

Tyr Gly Lys Pro Thr Gly Ala Gly Pro Asp Asp Asn Gly Gly Ala Cys
                30                  35                  40

Gly Tyr Lys Asp Val Asn Lys Ala Pro Phe Asn Ser Met Gly Ala Cys
            45                  50                  55

Gly Asn Leu Pro Ile Phe Lys Asp Gly Leu Gly Cys Gly Ser Cys Phe
        60                  65                  70

Glu Ile Lys Cys Asp Lys Pro Ala Glu Cys Ser Gly Glu Ala Val Val
    75                  80                  85

Val His Ile Thr Asp Met Asn Tyr Glu Gln Ile Ala Ala Tyr His Phe
90                  95                  100                 105

Asp Leu Ala Gly Thr Ala Phe Gly Ala Met Ala Lys Lys Gly Glu Glu
                110                 115                 120

Glu Lys Leu Arg Lys Ala Gly Ile Ile Asp Met Lys Phe Arg Arg Val
            125                 130                 135

Lys Cys Lys Tyr Gly Glu Lys Val Thr Phe His Val Glu Lys Gly Ser
        140                 145                 150

Asn Pro Asn Tyr Leu Ala Leu Leu Val Lys Tyr Val Asp Gly Asp Gly
    155                 160                 165

Asp Val Val Gly Val Asp Ile Lys Glu Lys Gly Gly Asp Ala Tyr Gln
170                 175                 180                 185

Pro Leu Lys His Ser Trp Gly Ala Ile Trp Arg Lys Asp Ser Asp Lys
                190                 195                 200
```

```
Pro  Ile  Lys  Phe  Pro  Val  Thr  Val  Gln  Ile  Thr  Thr  Glu  Gly  Gly  Thr
          205                      210                      215

Lys  Thr  Ala  Tyr  Glu  Asp  Val  Ile  Pro  Glu  Gly  Trp  Lys  Ala  Asp  Thr
          220                      225                      230

Thr  Tyr  Thr  Ala  Lys
          235
```

( 2 ) INFORMATION FOR SEQ ID NO:3:

( i ) SEQUENCE CHARACTERISTICS:
        ( A ) LENGTH: 1123 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 16..807

( i x ) FEATURE:
        ( A ) NAME/KEY: mat_peptide
        ( B ) LOCATION: 85..807

( x i ) SEQUENCE DESCRIPTION: SEQ ID NO:3:

```
CAAATTCAAG  ACAAG  ATG  GCG  TCC  TCC  TCG  TCG  GTG  CTC  CTG  GTG  GTG  GCG        51
                   Met  Ala  Ser  Ser  Ser  Ser  Val  Leu  Leu  Val  Val  Ala
                   -23            -20                      -15

CTG  TTC  GCC  GTG  TTC  CTG  GGC  AGC  GCG  CAT  GGC  ATC  GCG  AAG  GTA  CCA        99
Leu  Phe  Ala  Val  Phe  Leu  Gly  Ser  Ala  His  Gly  Ile  Ala  Lys  Val  Pro
     -10                 -5                      1                          5

CCG  GGC  CCC  AAC  ATC  ACG  GCC  GAG  TAC  GGC  GAC  AAG  TGG  CTG  GAC  GCG       147
Pro  Gly  Pro  Asn  Ile  Thr  Ala  Glu  Tyr  Gly  Asp  Lys  Trp  Leu  Asp  Ala
                    10                      15                           20

AAG  AGC  ACC  TGG  TAT  GGC  AAG  CCG  ACC  GGC  GCC  GGT  CCC  AAG  GAC  AAC       195
Lys  Ser  Thr  Trp  Tyr  Gly  Lys  Pro  Thr  Gly  Ala  Gly  Pro  Lys  Asp  Asn
                    25                      30                           35

GGC  GGC  GCG  TGC  GGG  TAC  AAG  GAC  GTT  GAC  AAG  GCG  CCG  TTC  AAC  GGC       243
Gly  Gly  Ala  Cys  Gly  Tyr  Lys  Asp  Val  Asp  Lys  Ala  Pro  Phe  Asn  Gly
                    40                      45                           50

ATG  ACC  GGC  TGC  GGC  AAC  ACC  CCC  ATC  TTC  AAG  GAC  GGC  CGT  GGC  TGC       291
Met  Thr  Gly  Cys  Gly  Asn  Thr  Pro  Ile  Phe  Lys  Asp  Gly  Arg  Gly  Cys
          55                      60                      65

GGC  TCC  TGC  TTC  GAG  ATC  AAG  TGC  ACC  AAG  CCC  GAG  TCC  TGC  TCC  GGC       339
Gly  Ser  Cys  Phe  Glu  Ile  Lys  Cys  Thr  Lys  Pro  Glu  Ser  Cys  Ser  Gly
70                  75                      80                              85

GAG  GCT  GTC  ACC  GTC  ACA  ATC  ACC  GAC  GAC  AAC  GAG  GAG  CCC  ATC  GCA       387
Glu  Ala  Val  Thr  Val  Thr  Ile  Thr  Asp  Asp  Asn  Glu  Glu  Pro  Ile  Ala
                    90                      95                          100

CCC  TAC  CAT  TTC  GAC  CTC  TCG  GGC  CAC  GCG  TTC  GGG  TCC  ATG  GCG  AAG       435
Pro  Tyr  His  Phe  Asp  Leu  Ser  Gly  His  Ala  Phe  Gly  Ser  Met  Ala  Lys
               105                      110                      115

AAG  GGC  GAG  GAG  CAG  AAG  CTC  CGC  AGC  GCC  GGC  GAG  CTG  GAG  CTC  CAG       483
Lys  Gly  Glu  Glu  Gln  Lys  Leu  Arg  Ser  Ala  Gly  Glu  Leu  Glu  Leu  Gln
          120                      125                      130

TTC  AGG  CGG  GTC  AAG  TGC  AAG  TAC  CCG  GAC  GGC  ACC  AAG  CCG  ACA  TTC       531
Phe  Arg  Arg  Val  Lys  Cys  Lys  Tyr  Pro  Asp  Gly  Thr  Lys  Pro  Thr  Phe
          135                      140                      145

CAC  GTC  GAG  AAG  GCT  TCC  AAC  CCC  AAC  TAC  CTC  GCT  ATT  CTG  GTG  AAG       579
His  Val  Glu  Lys  Ala  Ser  Asn  Pro  Asn  Tyr  Leu  Ala  Ile  Leu  Val  Lys
150                      155                      160                      165

TAC  GTC  GAC  GGC  GAC  GGT  GAC  GTG  GTG  GCG  GTG  GAC  ATC  AAG  GAG  AAG       627
Tyr  Val  Asp  Gly  Asp  Gly  Asp  Val  Val  Ala  Val  Asp  Ile  Lys  Glu  Lys
```

|   |   |   |   |   | 170 |   |   |   |   | 175 |   |   |   |   | 180 |   |     |
|---|---|---|---|---|---|---|---|---|---|---|---|---|---|---|---|---|-----|
| GGC | AAG | GAT | AAG | TGG | ATC | GAG | CTC | AAG | GAG | TCG | TGG | GGA | GCA | GTC | TGG | | 675 |
| Gly | Lys | Asp | Lys | Trp | Ile | Glu | Leu | Lys | Glu | Ser | Trp | Gly | Ala | Val | Trp | | |
|     |     | 185 |     |     |     |     |     | 190 |     |     |     |     | 195 |     |     | | |
| AGG | ATC | GAC | ACC | CCC | GAT | AAG | CTG | ACG | GGC | CCA | TTC | ACC | GTC | CGC | TAC | | 723 |
| Arg | Ile | Asp | Thr | Pro | Asp | Lys | Leu | Thr | Gly | Pro | Phe | Thr | Val | Arg | Tyr | | |
|     |     | 200 |     |     |     |     | 205 |     |     |     |     | 210 |     |     |     | | |
| ACC | ACC | GAG | GGC | GGC | ACC | AAA | TCC | GAA | GTC | GAG | GAT | GTC | ATC | CCT | GAG | | 771 |
| Thr | Thr | Glu | Gly | Gly | Thr | Lys | Ser | Glu | Val | Glu | Asp | Val | Ile | Pro | Glu | | |
|     | 215 |     |     |     |     | 220 |     |     |     |     | 225 |     |     |     |     | | |
| GGC | TGG | AAG | GCC | GAC | ACC | TCC | TAC | TCG | GCC | AAG | TGAGCAAGAA | | | GTGGAGTGAT | | | 824 |
| Gly | Trp | Lys | Ala | Asp | Thr | Ser | Tyr | Ser | Ala | Lys | | | | | | | |
| 230 |     |     |     |     | 235 |     |     |     |     | 240 |     |     |     |     |     | | |

```
CTTCTTCCAA  TCAGCTTAAT  TTTGACTCAA  GATCTCAAAT  AATCCAGCCG  CACATATATA     884
CGAGGCGGTG  AGACATACAA  GCTCCTCCAT  GAGTATATTC  ATTCATGCCG  TATAGAGAGG     944
AGAAAGATGC  CTGAATAAGA  GTTTGAGGTC  GACACCTTGT  GAGAAGTGTA  TATAGGAGGA    1004
ACCCAATCTG  GCTCCATCTT  TCTTTGCTCG  CACGGTGTAC  TGCTAAGGTT  ATCTTCTAAC    1064
AGGCCAGATT  AACCTACTAT  CTAATATATG  CAACGTATGG  TCATTTTCCC  TAAAAAAAA     1123
```

( 2 ) INFORMATION FOR SEQ ID NO:4:

( i ) SEQUENCE CHARACTERISTICS:
        ( A ) LENGTH: 263 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ala | Ser | Ser | Ser | Val | Leu | Leu | Val | Val | Ala | Leu | Phe | Ala | Val |
|---|---|---|---|---|---|---|---|---|---|---|---|---|---|---|
| -23 |  | -20 |  |  |  | -15 |  |  |  |  | -10 |  |  |  |
| Phe | Leu | Gly | Ser | Ala | His | Gly | Ile | Ala | Lys | Val | Pro | Pro | Gly | Pro | Asn |
|  |  | -5 |  |  |  |  | 1 |  |  |  | 5 |  |  |  |  |
| Ile | Thr | Ala | Glu | Tyr | Gly | Asp | Lys | Trp | Leu | Asp | Ala | Lys | Ser | Thr | Trp |
| 10 |  |  |  | 15 |  |  |  |  | 20 |  |  |  |  | 25 |  |
| Tyr | Gly | Lys | Pro | Thr | Gly | Ala | Gly | Pro | Lys | Asp | Asn | Gly | Gly | Ala | Cys |
|  |  |  | 30 |  |  |  |  |  | 35 |  |  |  |  | 40 |  |
| Gly | Tyr | Lys | Asp | Val | Asp | Lys | Ala | Pro | Phe | Asn | Gly | Met | Thr | Gly | Cys |
|  |  |  | 45 |  |  |  |  | 50 |  |  |  |  | 55 |  |  |
| Gly | Asn | Thr | Pro | Ile | Phe | Lys | Asp | Gly | Arg | Gly | Cys | Gly | Ser | Cys | Phe |
|  |  | 60 |  |  |  |  | 65 |  |  |  |  | 70 |  |  |  |
| Glu | Ile | Lys | Cys | Thr | Lys | Pro | Glu | Ser | Cys | Ser | Gly | Glu | Ala | Val | Thr |
|  | 75 |  |  |  |  | 80 |  |  |  |  | 85 |  |  |  |  |
| Val | Thr | Ile | Thr | Asp | Asp | Asn | Glu | Glu | Pro | Ile | Ala | Pro | Tyr | His | Phe |
| 90 |  |  |  |  | 95 |  |  |  |  | 100 |  |  |  |  | 105 |
| Asp | Leu | Ser | Gly | His | Ala | Phe | Gly | Ser | Met | Ala | Lys | Lys | Gly | Glu | Glu |
|  |  |  |  | 110 |  |  |  |  | 115 |  |  |  |  | 120 |  |
| Gln | Lys | Leu | Arg | Ser | Ala | Gly | Glu | Leu | Glu | Leu | Gln | Phe | Arg | Arg | Val |
|  |  |  | 125 |  |  |  |  |  | 130 |  |  |  | 135 |  |  |
| Lys | Cys | Lys | Tyr | Pro | Asp | Gly | Thr | Lys | Pro | Thr | Phe | His | Val | Glu | Lys |
|  |  | 140 |  |  |  |  | 145 |  |  |  |  | 150 |  |  |  |
| Ala | Ser | Asn | Pro | Asn | Tyr | Leu | Ala | Ile | Leu | Val | Lys | Tyr | Val | Asp | Gly |
|  | 155 |  |  |  |  | 160 |  |  |  |  | 165 |  |  |  |  |
| Asp | Gly | Asp | Val | Val | Ala | Val | Asp | Ile | Lys | Glu | Lys | Gly | Lys | Asp | Lys |
| 170 |  |  |  |  | 175 |  |  |  |  | 180 |  |  |  |  | 185 |
| Trp | Ile | Glu | Leu | Lys | Glu | Ser | Trp | Gly | Ala | Val | Trp | Arg | Ile | Asp | Thr |

```
                              190                     195                   200
Pro  Asp  Lys  Leu  Thr  Gly  Pro  Phe  Thr  Val  Arg  Tyr  Thr  Thr  Glu  Gly
                    205                     210                    215
Gly  Thr  Lys  Ser  Glu  Val  Glu  Asp  Val  Ile  Pro  Glu  Gly  Trp  Lys  Ala
                    220                     225                    230
Asp  Thr  Ser  Tyr  Ser  Ala  Lys
                    235            240
```

(2) INFORMATION FOR SEQ ID NO:5:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Ile  Ala  Lys  Val  Pro  Pro  Gly  Pro  Asn  Ile  Thr  Ala  Glu  Tyr  Gly  Asp
1                   5                        10                         15
Lys  Trp  Leu  Asp  Ala  Lys  Ser  Thr  Trp  Tyr  Gln
              20                       25
```

(2) INFORMATION FOR SEQ ID NO:6:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Ala  Met  Gln  Asp  Lys  Pro  Gly  Pro  Xaa  Ile  Thr  Ala  Thr  Tyr  Gly  Asp
1                   5                        10                         15
Lys  Trp  Leu  Asp  Ala  Lys  Ala  Thr  Phe  Tyr  Gln
              20                       25
```

(2) INFORMATION FOR SEQ ID NO:7:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

```
Pro  Pro  Lys  Val  Ala  Pro  Gly  Lys  Asn  Ile  Thr  Ala  Thr  Tyr  Gly  Ser
1                   5                        10                         15
Pro  Trp  Leu  Glu  Arg  Lys  Ala  Thr  Trp  Tyr  Gln
              20                       25
```

(2) INFORMATION FOR SEQ ID NO:8:

(i) SEQUENCE CHARACTERISTICS:
        (A) LENGTH: 28 amino acids
        (B) TYPE: amino acid
        (D) TOPOLOGY: linear (ii) MOLECULE TYPE: peptide ( v ) FRAGMENT TYPE: internal ( x i ) SEQUENCE DESCRIPTION: SEQ ID NO:8:

Tyr Thr Thr Glu Gly Gly Thr Lys Ser Glu Val Glu Asp Val Ile Pro
1               5                   10                      15

Glu Gly Trp Lys Ala Asp Thr Ser Tyr Ser Ala Lys
            20                  25

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:9:

Tyr Thr Thr Glu Gly Gly Thr Lys Ser Glu Ala Glu Asp Val Ile Pro
1               5                   10                      15

Glu Gly Trp Lys
            20

( 2 ) INFORMATION FOR SEQ ID NO:10:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:10:

Tyr Thr Thr Glu Gly Gly Thr Lys Ala Glu Ala Glu Asp Val Ile Pro
1               5                   10                      15

Glu Gly Trp Lys Ala Asp Thr Ser Tyr Glu
            20                  25

( 2 ) INFORMATION FOR SEQ ID NO:11:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

Tyr Thr Thr Glu Gly Gly Thr Lys Ala Glu Ala Glu Asp Val Ile Pro
1               5                   10                      15

Glu Gly Trp Lys Val Asp Thr Ser Tyr Glu
            20                  25

( 2 ) INFORMATION FOR SEQ ID NO:12:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Tyr  Thr  Thr  Glu  Gly  Gly  Lys  Lys  Val  Glu  Ala  Glu  Asp  Val  Ile  Pro
1                  5                        10                       15
Glu  Gly  Trp  Lys  Ala  Asp  Thr  Ser  Tyr  Glu
              20                       25
```

( 2 ) INFORMATION FOR SEQ ID NO:13:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Ile  Thr  Thr  Glu  Gly  Gly  Thr  Lys  Thr  Ala  Tyr  Glu  Asp  Val  Ile  Pro
1                  5                        10                       15
Glu  Gly  Trp  Lys  Ala  Asp  Thr  Thr  Tyr  Thr  Ala  Lys
              20                       25
```

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TCGCCACCCT TCTCCT                                              16

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CCTGTTGGCT TACCGTACCA                                     20

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CAACCTCCCC ATCTTCAA                                       18

( 2 ) INFORMATION FOR SEQ ID NO:17:

( i ) SEQUENCE CHARACTERISTICS:

```
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:17:

GGCGATTTGC TCGTAGTTCA T                                              21

( 2 ) INFORMATION FOR SEQ ID NO:18:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:18:

GGCATCATCG ACATGAAGTT C                                              21

( 2 ) INFORMATION FOR SEQ ID NO:19:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:19:

GCCAATCAAG TTTCCCGTCA                                                20

( 2 ) INFORMATION FOR SEQ ID NO:20:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:20:

GAACTTCATG TCGATGATGC C                                              21

( 2 ) INFORMATION FOR SEQ ID NO:21:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:21:

CTTGTCGCTG TCCTTCCTCC                                                20
```